United States Patent
Schultheiss et al.

(10) Patent No.: US 10,450,582 B2
(45) Date of Patent: *Oct. 22, 2019

(54) FUNGAL RESISTANT PLANTS EXPRESSING ACD

(71) Applicant: BASF PLANT SCIENCE COMPANY GMBH, Ludwigshafen (DE)

(72) Inventors: Holger Schultheiss, Boehl-Iggelheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,082

(22) Filed: Jun. 5, 2017

(65) Prior Publication Data

US 2017/0275647 A1 Sep. 28, 2017

Related U.S. Application Data

(63) Continuation of application No. 14/390,505, filed as application No. PCT/EP2013/055347 on Mar. 15, 2013, now Pat. No. 9,688,999.

(60) Provisional application No. 61/620,452, filed on Apr. 5, 2012.

(30) Foreign Application Priority Data

Apr. 5, 2012 (EP) ...................................... 12163265

(51) Int. Cl.
*C12N 15/82* (2006.01)
*C12N 9/88* (2006.01)

(52) U.S. Cl.
CPC ........... *C12N 15/8282* (2013.01); *C12N 9/88* (2013.01)

(58) Field of Classification Search
None
See application file for complete search history.

(56) References Cited

U.S. PATENT DOCUMENTS

| 5,512,466 | A | 4/1996 | Klee et al. |
| 8,097,769 | B2 | 1/2012 | Sarria-Millan et al. |
| 9,688,999 | B2 * | 6/2017 | Schultheiss ........ C12N 15/8282 |
| 2011/0265221 | A1 | 10/2011 | Abad et al. |
| 2014/0137284 | A1 | 5/2014 | Schultheiss et al. |

FOREIGN PATENT DOCUMENTS

| WO | WO-92/12249 A1 | 7/1992 |
| WO | WO-2007/011625 A2 | 1/2007 |
| WO | WO-2009/009142 A2 | 1/2009 |
| WO | WO-2009/039001 A1 | 3/2009 |
| WO | WO-2010/023491 A2 | 3/2010 |
| WO | WO-2012/023099 A1 | 2/2012 |
| WO | WO-2012/023111 A1 | 2/2012 |
| WO | WO-2012/172498 A1 | 12/2012 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/152917 A1 | 10/2013 |
| WO | WO-2014/024079 A2 | 2/2014 |
| WO | WO-2014/024090 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/117988 A1 | 8/2014 |
| WO | WO-2014/117990 A1 | 8/2014 |
| WO | WO-2014/118018 A1 | 8/2014 |

OTHER PUBLICATIONS

"1-Aminocyclopropane-1-Carboxylate Deaminase-Like Polypeptide DNA SEQ 320,", Database Geneseq [Online] XP002676305, retrieved from EBI accession No. GSN:AER48711, Database access.
"1-Aminocyclopropane-1-Carboxylate Deaminase-Like Polypeptide SEQ 321", Database Geneseq [On-line], retrieved from EBI accession No. GSP:AER48712, Database accession No. AER487.
European Search Report, issued in EP12163265, dated May 23, 2012.
Final Office Action for U.S. Appl. No. 14/390,505, dated Jun. 27, 2016, 10 pages.
Fourgoux-Nicol et al., "Isolation of Rapeseed Genes Expressed Early and Specifically During Development of the Male Gametophyte", Plant Molecular Biology, vol. 40, Issue 5, Jul. 1990.
Friedberg et al., Automated protein function prediction—the genomic challenge, Brief Bioinform, 7(3):225-42 (2006).
Guo et al. Protein Tolerance to Random Amino Acid Change, Proc. Natl. Acad. Sci. USA, 101(25):9205-10 (2004).
Heath, Cellular Interactions between Biotrophic Fungal Pathogens and Host or Nonhost Plants, Can. J. Plant Pathol., 24(3):259-62 (2002).
Hill, et al., Functional Analysis of Conserved Histidines in ADP-Glucose Pyrophosphorylase from *Escherichia coli*, Biochem. Biophys. Res. Commun., 244(2):573-7 (1998).

(Continued)

*Primary Examiner* — Medina A Ibrahim
(74) *Attorney, Agent, or Firm* — Marshall, Gerstein & Borun LLP

(57) ABSTRACT

The present invention relates to a method of increasing resistance against fungal pathogens of the family Phacosporaceae in plants and/or plant cells. This is achieved by increasing the expression of an ACD protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the family Phacopsoraceae, and to recombinant expression vectors comprising a sequence that is identical or homologous to a sequence encoding an ACD protein.

16 Claims, 6 Drawing Sheets

Specification includes a Sequence Listing.

(56) References Cited

OTHER PUBLICATIONS

International Preliminary Report on Patentability for PCT Patent Application No. PCT/EP2013/055347, dated Oct. 16, 2014.
International Search Report, International Application No. PCT/EP2013/055347, dated May 23, 2013.
Klee et al., Control of ethylene synthesis by expression of a bacterial enzyme in transgenic tomato plants, Plant Cell, 3911):1187-93 (1991).
McDonnell et al., Ethylene levels are regulated by a plant encoded 1-aminocyclopropane-1-carboxylic acid deaminase, Physiol. Plant, 136(1):94-109 (2009).
Neu et al., Cytological and molecular analysis of the Hordeum vulgare-Puccinia triticina nonhost interaction, Mol. Plant Microbe Interact., 16(7):626-33 (2003).
Non Final Office Action for U.S. Appl. No. 14/390,505, dated Dec. 14, 2015, 23 pages.
Notice of Allowance for U.S. Appl. No. 14/390,505, dated Feb. 23, 2017, 7 pages.
Rytter et al., Additional Alternative Hosts of Phakopsora Pachyrhizi, Causal Agent of Soybean Rust, Plant Disease, 68(9):818-9 (1984).
Sinclair, et al. eds., Proceedings of the Soybean Rust Workshop, Aug. 9-11, 1995. Urbana, IL: National Soybean Research Laboratory (1995).

* cited by examiner

Figure 3:

```
   1 ATGAACCTTA ACAGATTCGA GAGATACCCA CTTACTTTCG GACCATCTCC
  51 AATTACTCCA CTTAAGAGGC TTTCTCAGCA TCTTGGAGGA AAGGTTGAGC
 101 TTTACGCTAA GAGAGAGGAT TGCAACTCTG GACTTGCTTT CGGAGGAAAC
 151 AAGACTAGAA AGCTCGAGTA CCTTATTCCA GAGGCTATTG AGCAAGGATG
 201 CGATACCCTT GTTTCCATTG GAGGAATTCA GTCTAACCAG ACCAGACAAG
 251 TTGCTGCTGT TGCTGCACAT CTTGGAATGA AGTGCGTTTT GGTGCAAGAA
 301 AACTGGGTGA ACTACTCTGA TGCTGTTTAC GATAGGGTGG AAACATTGA
 351 GATGTCCAGG ATTATGGGAG CTGATGTTAG ACTTGATGCT GCTGGATTCG
 401 ATATTGGAAT TAGGCCATCT TGGGAGAAGG CTATGTCTGA TGTTGTTGAG
 451 CAAGGTGGAA AGCCATTCCC AATTCCAGCT GGATGCTCTG AACATCCATA
 501 TGGTGGACTT GGATTCGTTG GATTTGCTGA AGAGGTTAGG CAACAAGAGA
 551 AAGAGCTTGG CTTCAAGTTC GATTACATTG TGGTTTGCTC TGTTACTGGA
 601 TCTACTCAGG CTGGAATGGT TGTTGGATTC GCTGCTGATG AAGGTCTAA
 651 GAACGTGATC GGAATTGATG CTTCTGCTAA GCCAGAACAA ACTAAGGCTC
 701 AGATTCTCAG GATTGCTAGA CATACTGCTG AGCTTGTTGA ACTCGGAAGA
 751 GAGATTACTG AAGAGGACGT TGTGCTTGAT ACCAGATTCG CTTATCCAGA
 801 GTACGGACTT CCAAACGAGG GAACTCTTGA GGCTATTAGG CTTTGCGGAT
 851 CTCTTGAAGG TGTTCTTACC GATCCAGTTT ACGAGGGAAA GTCTATGCAT
 901 GGAATGATTG AGATGGTTAG AAGGGGAGAA TTCCCAGAAG GATCCAAGGT
 951 TCTCTATGCT CATCTTGGAG GTGCTCCAGC TCTTAACGCT TACTCATTCC
1001 TCTTCAGGAA CGGCTAA
```

Figure 4:

```
MNLNRFERYPLTFGPSPITPLKRLSQHLGGKVELYAKREDCNSGLAFGGN 50
KTRKLEYLIPEAIEQGCDTLVSIGGIQSNQTRQVAAVAAHLGMKCVLVQE 100
NWVNYSDAVYDRVGNIEMSRIMGADVRLDAAGFDIGIRPSWEKAMSDVVE 150
QGGKPFPIPAGCSEHPYGGLGFVGFAEEVRQQEKELGFKFDYIVVCSVTG 200
STQAGMVVGFAADGRSKNVIGIDASAKPEQTKAQILRIARHTAELVELGR 250
EITEEDVVLDTRFAYPEYGLPNEGTLEAIRLCGSLEGVLTDPVYEGKSMH 300
GMIEMVRRGEFPEGSKVLYAHLGGAPALNAYSFLFRNG*
```

Figure 6:

| SEQ ID NO: | Description of the sequence listing |
|---|---|
| 1 | Nucleotide sequence; full-length-sequence of the ACD-gene; Pseudomonas spec. |
| 2 | Amino acid sequence; ACD-protein; Pseudomonas spec. |
| 3 | Nucleotide sequence ACD, variant 1 |
| 4 | Nucleotide sequence ACD, variant 2 |
| 5 | Nucleotide sequence ACD, variant 3 |
| 6 | Nucleotide sequence ACD, variant 4 |
| 7 | Nucleotide sequence ACD, variant 5 |
| 8 | Nucleotide sequence ACD, variant 6 |
| 9 | Nucleotide sequence ACD, variant 7 |
| 10 | Nucleotide sequence ACD, variant 8 |
| 11 | Nucleotide sequence ACD, variant 9 |
| 12 | Amino acid sequence ACD, variant 9 |
| 13 | Nucleotide sequence ACD, variant 10 |
| 14 | Amino acid sequence ACD, variant 10 |
| 15 | Nucleotide sequence ACD, variant 11 |
| 16 | Amino acid sequence ACD, variant 11 |
| 17 | Nucleotide sequence ACD, variant 12 |
| 18 | Amino acid sequence ACD, variant 12 |
| 19 | Nucleotide sequence ACD, variant 13 |
| 20 | Amino acid sequence ACD, variant 13 |
| 21 | Nucleotide sequence ACD, variant 14 |
| 22 | Amino acid sequence ACD, variant 14 |

Figure 6 continued:

| 23 | Nucleotide sequence ACD, variant 15 |
|---|---|
| 24 | Amino acid sequence ACD, variant 15 |
| 25 | Nucleotide sequence ACD, variant 16 |
| 26 | Amino acid sequence ACD, variant 16 |

SEQUENCE LISTING

```
<160> NUMBER OF SEQ ID NOS: 26

<210> SEQ ID NO 1
<211> LENGTH: 1017
<212> TYPE: DNA
<213> ORGANISM: Pseudomonas spec.

<400> SEQUENCE: 1
atgaacctta acagattcga gagataccca cttactttcg gaccatctcc aattactcca      60
cttaagaggc tttctcagca tcttggagga aaggttgagc tttacgctaa gagagaggat     120
tgcaactctg gacttgcttt cggaggaaac aagactagaa agctcgagta ccttattcca     180
gaggctattg agcaaggatg cgataccctt gtttccattg gaggaattca gtctaaccag     240
```

```
accagacaag ttgctgctgt tgctgcacat cttggaatga agtgcgtttt ggtgcaagaa      300
aactgggtga actactctga tgctgtttac gatagggtgg aaacattgat gatgtccagg      360
attatgggag ctgatgttag acttgatgct gctggattcg atattggaat taggccatct      420
tgggagaagg ctatgtctga tgttgttgag caaggtggaa agccattccc aattccagct      480
ggatgctctg aacatccata tggtggactt ggattcgttg gatttgctga gagggttagg      540
caacaagaga aagagcttgg cttcaagttc gattacattt ggttttgctc tgttactgga      600
tctactcagg ctggaatggt tgttggattc gctgctgatg aaggtctaa gaacgtgatc       660 ggaattgatg cttctgctaa gccagaacaa actaaggctc agattctcag gattgctaga      720
catactgctg agcttgttga actcggaaga gagattactg aagaggacgt tgtgcttgat      780
accagattcg cttatccaga gtacggactt ccaaacgagg gaactcttga ggctattagg      840
ctttgcggat ctcttgaagg tgttcttacc gatccagttt acgagggaaa gtctatgcat      900
ggaatgattg agatggttag aaggggagaa ttcccagaag gatccaaggt tctctatgct      960
catcttggag gtgctccagc tcttaacgct tactcattcc tcttcaggaa cggctaa       1017
```

<210> SEQ ID NO 2
<211> LENGTH: 338
<212> TYPE: PRT
<213> ORGANISM: Pseudomonas spec.

<400> SEQUENCE: 2

Met Asn Leu Asn Arg Phe Glu Arg Tyr Pro Leu Thr Phe Gly Pro Ser
1               5                  10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
        35                  40                  45

Gly Asn Lys Thr Arg Lys Leu Glu Tyr Leu Ile Pro Glu Ala Ile Glu
    50                  55                  60

Gln Gly Cys Asp Thr Leu Val Ser Ile Gly Gly Ile Gln Ser Asn Gln
65                  70                  75                  80

Thr Arg Gln Val Ala Ala Val Ala Ala His Leu Gly Met Lys Cys Val
                85                  90                  95

Leu Val Gln Glu Asn Trp Val Asn Tyr Ser Asp Ala Val Tyr Asp Arg
            100                 105                 110

Val Gly Asn Ile Glu Met Ser Arg Ile Met Gly Ala Asp Val Arg Leu
        115                 120                 125

Asp Ala Ala Gly Phe Asp Ile Gly Ile Arg Pro Ser Trp Glu Lys Ala
    130                 135                 140

Met Ser Asp Val Val Glu Gln Gly Gly Lys Pro Phe Pro Ile Pro Ala
145                 150                 155                 160

Gly Cys Ser Glu His Pro Tyr Gly Gly Leu Gly Phe Val Gly Phe Ala
                165                 170                 175

Glu Glu Val Arg Gln Gln Glu Lys Glu Leu Gly Phe Lys Phe Asp Tyr
            180                 185                 190

Ile Val Val Cys Ser Val Thr Gly Ser Thr Gln Ala Gly Met Val Val
        195                 200                 205

Gly Phe Ala Ala Asp Gly Arg Ser Lys Asn Val Ile Gly Ile Asp Ala
    210                 215                 220

Ser Ala Lys Pro Glu Gln Thr Lys Ala Gln Ile Leu Arg Ile Ala Arg
225                 230                 235                 240

-continued

His Thr Ala Glu Leu Val Glu Leu Gly Arg Glu Ile Thr Glu Glu Asp
                245                 250                 255

Val Val Leu Asp Thr Arg Phe Ala Tyr Pro Glu Tyr Gly Leu Pro Asn
            260                 265                 270

Glu Gly Thr Leu Glu Ala Ile Arg Leu Cys Gly Ser Leu Glu Gly Val
        275                 280                 285

Leu Thr Asp Pro Val Tyr Glu Gly Lys Ser Met His Gly Met Ile Glu
    290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                325                 330                 335

Asn Gly

<210> SEQ ID NO 3
<211> LENGTH: 1017
<212> TYPE: DNA
<213> ORGANISM: Artificial sequence
<220> FEATURE:
<223> OTHER INFORMATION: Sequence variant 1

<400> SEQUENCE: 3
atgaatctaa atcggtttga acgttatccc ctgacgtttg gcccgagccc gatcaccccc      60
ttgaaacgtc tgtcgcaaca cttgggtggg aaagtagaac tgtatgcgaa acgagaagac     120
tgtaattcgg gtctggcgtt tggaggaaat aaaacgcgaa aactggaata tctgatcccc     180
gaagcaatag aacagggctg tgacacattg gtgagcatag ggggtatcca atccaatcaa     240
actcgccagg tcgccgcggt cgccgcccac ctcgggatga atgtgtcat ggttcaggag      300 aattgggtta actattcgga cgctgtgtat gaccgcgtcg gcaatatcga atgtccaga     360 ataatgggtg ccgacgttag gctgacgcg cggggttttg acatcgggat caggccgtcg     420
tgggaaaaag ccatgtccga cgtagtcgaa cagggcggta aaccgtttcc tatacctgct     480
ggctgttctg agcacccgta cggggtttta ggctttgtgg gtttcgcaga agaagtgagg     540
cagcaggaaa aggaactcgg ttttaaattt gactatatag ttgtgtgttc ggttacgggc     600
agtacgcaag ccgggatggt ggtgggtttt gcggcagacg gccgcagcaa aaatgttatt     660
ggaatcgacg cgtcagccaa accagagcag acaaaggcac aaatcttaag aattgcaagg     720
cacacagccg aactcgtcga gctgggtcgt gaaatcaccg aggaagatgt cgtactagac     780
actaggtttg cgtacccgga atatgggtta cctaatgaag aactcttga agcaatccgg      840 ctatgtggtt cactcgaggg agtgttgact gaccccgttt atgaagggaa atccatgcac     900
gggatgatcg aaatggtacg acggggagag tttccggagg ggtcaaaagt gctttacgcg     960
cacctgggcg gagccccggc gcttaatgcg tatagctttt tgtttcgaaa tgggtga      1017

<210> SEQ ID NO 4
<211> LENGTH: 1017
<212> TYPE: DNA
<213> ORGANISM: Artificial sequence
<220> FEATURE:
<223> OTHER INFORMATION: Sequence variant 2

<400> SEQUENCE: 4
atgaacctca atcggtttga gcggtatcct ttaacgtttg gaccttcccc cattacaccg      60
cttaagagac taagtcagca ccttggcggg aaggtggagc tgtacgcgaa acgggaagac     120

```
tgcaatagtg gactcgcatt cggggggcaat aaaacccgaa agttagaata cctgattcct      180
gaagctatag agcagggttg tgatacgttg gtgtcaatcg gcgggatcca atctaatcaa      240
actcgtcaag tcgctgccgt agcggctcat ttaggtatga aatgcgttat ggttcaggag      300
aattgggtta attatagtga tgcagtttat gaccgcgtag ggaatataga aatgtctagg      360
ataatgggtg ccgacgttcg actggacgct gcggggttcg acatcgggat aaggccctcc      420
tgggaaaaag caatgagcga cgtcgtagag caggggggga aaccttttcc tatcccagcg      480
ggatgctcgg agcacccgta tgggggttta gggttcgtag gcttcgccga ggaagtgaga      540
cagcaggaga aagaacttgg ctttaaattt gattatattg tagtatgttc ggtgacgggg      600
tcaacgcaag ctgggatggt ggtgggattc gccgcggatg gacgaagtaa aaatgtcata      660
ggaattgacg catcggctaa acccgagcag accaaagcac aaatactgag aatcgcccgg      720
cacaccgccg aactggtcga gcttggtcgt gaaattacgg aggaagatgt cgtcctagac      780
actaggtttg cttaccctga atatgggcta ccaaatgagg gcactcttga agcaattcgt      840
ctgtgtggaa gcctagaagg cgtccttact gatcccgtct atgaaggcaa gtccatgcac      900
ggcatgatcg aaatggtacg tagaggggag tttcccgagg gttctaaagt attatacgct      960
catctcgggg gcgcaccggc acttaatgct tactccttct tatttcggaa tggctaa       1017

<210> SEQ ID NO 5
<211> LENGTH: 1017
<212> TYPE: DNA
<213> ORGANISM: Artificial sequence
<220> FEATURE:
<223> OTHER INFORMATION: Sequence variant 3

<400> SEQUENCE: 5
atgaatctga acagatttga acgttatccg ctgacattcg gccctagccc cattacgcca       60
cttaagcggc tttcccaaca tctaggtgga aaggtagaac tctatgctaa gagagaagat      120
tgcaactcgg gacttgcgtt cggggggtaac aagacaagaa agttggaata cctaatacca      180
gaagctatcg aacaagggtg cgacactctt gtttctattg gaggaataca aagtaaccag      240
accagacaag ttgcagcagt ggcggcacat cttggaatga aatgcgtaat ggttcaggag      300
aactgggtga actattccga cgccgtctac gatagggttg ggaatataga gatgtcccga      360
atcatggggg ctgatgttag attggacgcc gccggctttg acattggcat tcggccttct      420
tgggagaaag cgatgtcaga cgtagttgag cagggcggaa agccttttccc gatacctgcc      480 ggatgctccg agcacccctta cggtgggcta ggatttgtgg gattcgcaga ggaagttcgt      540
caacaggaga aggaacttgg cttcaaattc gactatatag tcgtatgttc tgtaacaggc      600
agcacgcaag caggcatggt tgtaggtttt gctgctgatg ggcgttctaa aaatgtaata      660
ggcatagacg cgtctgcgaa accagagcaa actaaagccc aaattctccg tatcgcaaga      720
catacggccg aactggttga gttaggcagg gagatcaccg aggaagatgt ggtactggac      780
accagattcg cgtaccccga atatggacta ccgaacgagg gaacacttga ggcgattagg      840
ctatgcggat ccttggaagg tgtgcttacg gacccagtat atgagggtaa atccatgcat      900
ggtatgattg agatggtgag aagggggagaa tttccggagg gtagcaaagt tctttacgca      960
cacttaggtg gggcaccagc ccttaacgct tattctttc tatttcggaa tggatag      1017

<210> SEQ ID NO 6
<211> LENGTH: 1017
<212> TYPE: DNA
<213> ORGANISM: Artificial sequence
```

<220> FEATURE:
<223> OTHER INFORMATION: Sequence variant 4

<400> SEQUENCE: 6

| | | | | | |
|---|---|---|---|---|---|
| atgaacctaa | atagattcga | gaggtaccca | cttacgtttg | gtccatctcc | aattactcca | 60 |
| ctcaaacgtc | tttctcaaca | tttgggcggg | aaggttgagc | tttatgccaa | gagagaggac | 120 |
| tgcaattccg | ggcttgcttt | cggagggaat | aagactagaa | agttagagta | tcttattcca | 180 |
| gaagctatag | aacaggggtg | cgatacgctg | gtatccattg | gcggtattca | atctaatcaa | 240 |
| acaagacaag | tcgccgccgt | agcagcgcat | ttggggatga | agtgtgtctt | ggttcaagaa | 300 |
| aattgggtga | actactccga | tgctgtttac | gaccgtgtcg | gtaacattga | aatgtccaga | 360 |
| ataatggggg | ctgacgttag | acttgacgct | gcgggcttcg | atatcgggat | aaggcctagt | 420 |
| tgggagaaag | ctatgtctga | cgttgttgag | caaggtggaa | agccgttccc | aattccagcc | 480 |
| ggttgttctg | agcatccata | tggtggactt | gggtttgttg | gattcgcaga | ggaagtacgg | 540 |
| caacaagaga | aagagcttgg | atttaaattc | gactatatcg | tagtttgcag | cgtgactggc | 600 |
| tcgactcagg | ctggaatggt | ggttggattt | gctgctgacg | gacgcagtaa | aaatgtaatt | 660 |
| gggattgacg | cgtctgccaa | acccgaacag | actaaagctc | agatcttgag | gatagctcgg | 720 |
| cacactgcgg | agcttgttga | gctaggccgg | gagattaccg | aagaggatgt | ggtacttgac | 780 |
| acccgttttg | cgtatccaga | gtacgggcta | ccaaacgagg | gaactcttga | agccattcga | 840 |
| ctctgtggat | cactcgaagg | tgttcttact | gacccggttt | acgagggaaa | aagcatgcac | 900 |
| ggaatgattg | aaatggttag | acgcggagaa | ttcccagagg | gctccaaggt | gctctatgct | 960 |
| caccttggag | gtgctccagc | tctgaacgcg | tactcgttcc | tcttcaggaa | cggctga | 1017 |

<210> SEQ ID NO 7
<211> LENGTH: 1017
<212> TYPE: DNA
<213> ORGANISM: Artificial sequence
<220> FEATURE:
<223> OTHER INFORMATION: Sequence variant 5

<400> SEQUENCE: 7

| | | | | | |
|---|---|---|---|---|---|
| atgaacctta | atagattcga | gagatacccg | ttgaccttcg | gaccaagtcc | aattactcca | 60 |
| cttaagaggc | tttcgcaaca | tcttggtgga | aaggttgaac | tttacgctaa | aagggaggat | 120 |
| tgtaactctg | gtcttgcttt | cggaggaaac | aagactagaa | aactcgagta | tcttattcca | 180 |
| gaggccatcg | agcaaggatg | cgatactctt | gtgtccatag | gaggaatcca | atctaaccaa | 240 |
| accagacaag | ttgctgctgt | tgctgcccac | ttgggaatga | agtgcgttat | ggtgcaagaa | 300 |
| aattgggtca | actattctga | cgctgtttac | gatcgagtcg | gaaacataga | aatgtcaagg | 360 |
| ataatgggag | cggacgttag | acttgatgct | gcaggatttg | acattggaat | taggccatct | 420 |
| tgggagaagg | ctatgtctga | tgtcgttgag | caaggtggaa | agccattccc | catccccgct | 480 |
| ggttgttctg | aacatccata | tggtggactg | ggattcgttg | gattcgcaga | agaggttagg | 540 |
| caacaagaaa | aagagctcgg | atttaagttc | gactacattg | tggtgtgctc | tgttactgga | 600 |
| agcacgcagg | ctggaatggt | tgttggattt | gctgcggatg | gacggtctaa | gaacgtgatc | 660 |
| ggaattgatg | cttctgcaaa | gccagaacag | actaaagctc | aaattctcag | gattgctcgc | 720 |
| catactgcag | agctagttga | gctgggacgg | gaaataacag | aagaggacgt | tgtgcttgac | 780 |
| acccgattcg | cttatccaga | atacggcttg | ccgaatgaag | gtacgcttga | ggctattagg | 840 |
| ctttgcggat | cgctcgaagg | tgttcttacc | gatccagttt | acgagggaaa | gtctatgcat | 900 |

| | |
|---|---|
| ggaatgatag aaatggttcg gagggggaa ttcccggagg aagcaaggt gttatatgct | 960 |
| catcttggag gagccccagc gcttaacgct tactcgttcc tattcaggaa cggctga | 1017 |

<210> SEQ ID NO 8
<211> LENGTH: 1017
<212> TYPE: DNA
<213> ORGANISM: Artificial sequence
<220> FEATURE:
<223> OTHER INFORMATION: Sequence variant 6

<400> SEQUENCE: 8

| | |
|---|---|
| atgaaccta atagatttga aagataccca cttactttcg gaccctcacc aatcactcca | 60 |
| cttaagaggc tttcacagca tcttggagga aaggttgaac tttacgctaa gagagaagat | 120 |
| tgtaattctg gattggcttt tggaggaaac aagactagaa agctcgaata tctcatacca | 180 |
| gaggctatcg agcagggatg cgataccctt gtttcgattg gaggaattca atctaaccag | 240 |
| accagacaag ttgctgctgt tgcagctcat cttggaatga agtgcgttat ggtgcaagaa | 300 |
| aactgggtca attactctga cgctgtttac gatagggtag gaaacattga atgtccagg | 360 |
| attatgggag ctgatgttag acttgacgct gctggattcg atataggaat taggccatct | 420 |
| tgggagaagg ctatgtctga tgttgtcgaa caggggggaa agccattccc aattcctgct | 480 |
| ggatgcagcg aacatccata tggtggactt ggatttgttg gatttgctga ggaggttagg | 540 |
| cagcaagaga aagaacttgg gtttaagttc gattatattg ttgtttgctc agttactggg | 600 |
| tctacccaag ctggaatggt tgttggattt gctgctgatg caggtctaa gaacgtgatc | 660 |
| ggaattgatg cctctgctaa gccggaacaa actaaggctc agattctcag aattgctaga | 720 |
| catactgctg agctagttga gctcggaaga gagattactg aagaggacgt ggtgcttgat | 780 |
| accagattcg cttatccaga atacggactt ccaaacgaag gaactcttga agcaattagg | 840 |
| ctgtgtggct ctcttgaggg tgttcttacc gaccccgttt acgaaggaaa gtctatgcat | 900 |
| ggaatgattg aaatggtccg cagggagag ttcccagagg aagtaaggt attgtatgcc | 960 |
| catcttggag gagctcccgc tctcaacgcg tactcattcc tcttcaggaa cggctga | 1017 |

<210> SEQ ID NO 9
<211> LENGTH: 1017
<212> TYPE: DNA
<213> ORGANISM: Artificial sequence
<220> FEATURE:
<223> OTHER INFORMATION: Sequence variant 7

<400> SEQUENCE: 9

| | |
|---|---|
| atgaacctaa acagattcga aagataccca cttactttcg gaccatctcc aattactcca | 60 |
| cttaaaaggc ttagccagca cctaggagga aaggttgagc tttatgctaa agagagaggat | 120 |
| tgcaactctg gacttgcctt cggcggaaac aagactagaa agctcgaata ccttattcca | 180 |
| gaggctattg agcaaggatg cgatacgctt gtttccattg gaggaataca gtctaaccag | 240 |
| accagacaag ttgctgctgt tgctgcacat cttggaatga aatgcgttat ggttcaagaa | 300 |
| aactgggtga actactcgga tgctgtttac gatagggtgg gaaacattga gatgtcccgt | 360 |
| attatgggag ctgatgtgag acttgatgct gctggattcg atattggaat acggccatct | 420 |
| tgggagaagg ctatgtctga tgttgttgag caaggtggca agccattccc aatcccagca | 480 |
| ggatgctcag aacacccata tggtggactt ggattcgttg gattcgctga gaggttcgc | 540 |
| caacaagaga aagagcttgg tttcaagttc gattacatag tggtttgctc tgttactgga | 600 |
| tctactcaag ctggaatggt tgttggattt gctgctgatg aaggtctaa gaacgtgatc | 660 |

```
ggaattgatg cttctgctaa gccagaacag acgaaggctc agattttaag gattgcaaga    720
catactgctg agcttgttga actcggaaga gagattactg aagaggacgt tgtgcttgat    780
accagattcg catacccaga gtatggactt ccgaacgagg gaactcttga ggccattagg    840
ctttgcggtt ctcttgaagg tgttcttacc gatccagttt acgaaggaaa gtctatgcat    900
ggaatgattg agatggttag aaggggtgaa ttccctgaag gctccaaggt tctctatgct    960
catcttggag gtgctccagc acttaacgct tacagtttcc ttttcaggaa cgggtag     1017
```

<210> SEQ ID NO 10  
<211> LENGTH: 1017  
<212> TYPE: DNA  
<213> ORGANISM: Artificial sequence  
<220> FEATURE:  
<223> OTHER INFORMATION: Sequence variant 8

<400> SEQUENCE: 10

```
atgaacctta atagattcga gagataccca cttactttcg gaccatctcc aattactcca     60
cttaagaggc tttctcagca tcttggagga aaggttgagc tttacgccaa gcgcgaggat    120
tgcaactcgg gactcgcttt cggaggaaac aagactagaa agctcgagta ccttattcca    180
gaggctattg agcaaggatg cgatacccta gtttccatcg gaggaattca gtctaaccag    240
accagacagg ttgcggctgt tgctgcgcat cttggaatga agtgcgttat ggtgcaagaa    300
aactgggtga actactctga tgcagtttat gatagggtgg aaacattga dgatgtccagg    360 attatgggag ctgatgtgag acttgacgct gctggattcg atattggcat taggccatct    420
tgggagaagg ctatgtctga tgttgttgag caaggtggaa agccattccc aattccagct    480
ggatgttctg agcatccata tggtggactt gggttcgttg gatttgctga agaggttagg    540
cagcaggaga aggagcttgg attcaagttc gattacattg tggtttgctc tgttactgga    600
tctactcagg ccggaatggt tgttggattc gctgctgatg aaggtctaa gaacgtgatc    660 ggaattgatg cttctgctaa gccagaacaa actaaggctc agattctcag gattgcaaga    720
catactgctg agcttgttga actcggaaga gagattactg aagaggacgt tgtgcttgat    780
accagattcg cgtatccaga gtacggactt ccaaacgagg gaactcttga ggctattagg    840
ctttgcggat ctcttgaagg tgtccttacc gatccagttt acgaaggaaa gtctatgcat    900
ggaatgattg agatggtcag aaggggagag ttcccggaag gatccaaggt tctctatgct    960
catcttggag gtgctccagc tcttaacgct tactcattcc tcttcaggaa cggctaa     1017
```

<210> SEQ ID NO 11  
<211> LENGTH: 1014  
<212> TYPE: DNA  
<213> ORGANISM: Artificial sequence  
<220> FEATURE:  
<223> OTHER INFORMATION: Nucleotide sequence ACD, variant 9

<400> SEQUENCE: 11

```
atgcagctga acagattcga gagatacccc atgagcttcg ccccagcccc catcaccccc     60
ctgaagagac tgagccagca cctgggcggc aaggtggagc tgtacgccaa gagagaggac    120
tgcaacagcg gctggccttt cggcggcaac aagaccagaa gaatggagta cgccatcccc    180
gacgccgccg agcagggctg cgagaccgtg gtgtgcatcg gcgccatcaa cagcaaccag    240
accaagcagg tgatggccgg cgccggcaga ggcctgatga gagcgtgct ggtgaacgag    300 cagtggatca actacaccga catcgtgtgg gaccacgtgt gaacatcga gatgagcaga    360
```

```
atcatgctgg ccgaggtgag aatggaggcc gtgggctggg agctgggcgt gagaccctgc    420
tgggagaagg tgatcagcga catcgtggag cagggcctgc accccctggcc catccccctg   480
atgaccagcg acagacccctt cggcatgatc ggcttcatcg gcttcgccga cgaggcccac   540
cagcaggaca aggagctggc cttccacttc gagtacatgg ccgtgtgcac catctgcggc   600
agctgccagg ccatcgtggt gctgggcttc gccgccgacg tgagaagcaa gcagatgatg   660
ggcgccgacg ccagcatcaa gcccgacaac acccacatcc agatcctgag aatcgcccac   720
cacaccggcg agggcatgga gatcggcaag gagatctgcg acgaggacat catgctggag   780
accagattca tgtaccccga gtacggcatg cccaacgaga tcaccctgga gatgatcaga   840
ctgtgcggca gcctggaggg cgtgctgacc gaccccgtgt acgagggcaa gagcatgcac   900
ggcatgatcg agatggtgag aagaggcgag ttccccgagg gcagcaaggt gctgtacgcc   960
cacctgggcg gcgcccccgc cctgaacgcc tacagcttcc tgttcagaaa cggc         1014
```

<210> SEQ ID NO 12
<211> LENGTH: 338
<212> TYPE: PRT
<213> ORGANISM: Artificial sequence
<220> FEATURE:
<223> OTHER INFORMATION: Amino acid sequence ACD, variant 9

<400> SEQUENCE: 12

```
Met Gln Leu Asn Arg Phe Glu Arg Tyr Pro Met Ser Phe Gly Pro Ser
1               5                   10                  15
Pro Ile Thr Pro Leu Lys Arg Leu Ser Gln His Leu Gly Gly Lys Val
            20                  25                  30
Glu Leu Tyr Ala Lys Arg Glu Asp Cys Asn Ser Gly Leu Ala Phe Gly
        35                  40                  45
Gly Asn Lys Thr Arg Arg Met Glu Tyr Ala Ile Pro Asp Ala Ala Glu
    50                  55                  60
Gln Gly Cys Glu Thr Val Val Cys Ile Gly Ala Ile Asn Ser Asn Gln
65                  70                  75                  80
Thr Lys Gln Val Met Ala Gly Ala Gly Arg Gly Leu Met Lys Ser Val
                85                  90                  95
Leu Val Asn Glu Gln Trp Ile Asn Tyr Thr Asp Ile Val Trp Asp His
            100                 105                 110
Val Val Asn Ile Glu Met Ser Arg Ile Met Leu Ala Glu Val Arg Met
        115                 120                 125
Glu Ala Val Gly Trp Glu Leu Gly Val Arg Pro Cys Trp Glu Lys Val
    130                 135                 140
Ile Ser Asp Ile Val Glu Gln Gly Leu His Pro Trp Pro Ile Pro Leu
145                 150                 155                 160
Met Thr Ser Asp Arg Pro Phe Gly Met Ile Gly Phe Ile Gly Phe Ala
                165                 170                 175
Asp Glu Ala His Gln Gln Asp Lys Glu Leu Ala Phe His Phe Glu Tyr
            180                 185                 190
Met Ala Val Cys Thr Ile Cys Gly Ser Cys Gln Ala Ile Val Val Leu
        195                 200                 205
Gly Phe Ala Ala Asp Val Arg Ser Lys Gln Met Met Gly Ala Asp Ala
    210                 215                 220
Ser Ile Lys Pro Asp Asn Thr His Ile Gln Ile Leu Arg Ile Ala His
225                 230                 235                 240
His Thr Gly Glu Gly Met Glu Ile Gly Lys Glu Ile Cys Asp Glu Asp
                245                 250                 255
```

```
Ile Met Leu Glu Thr Arg Phe Met Tyr Pro Glu Tyr Gly Met Pro Asn
            260                 265                 270

Glu Ile Thr Leu Glu Met Ile Arg Leu Cys Gly Ser Leu Glu Gly Val
        275                 280                 285

Leu Thr Asp Pro Val Tyr Glu Gly Lys Ser Met His Gly Met Ile Glu
    290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                325                 330                 335

Asn Gly
```

<210> SEQ ID NO 13
<211> LENGTH: 1014
<212> TYPE: DNA
<213> ORGANISM: Artificial sequence
<220> FEATURE:
<223> OTHER INFORMATION: Nucleotide sequence ACD, variant 10

<400> SEQUENCE: 13

```
atgaacgtgc agagatacga cagataccc ctgagcttcc tgcccagccc catcacccc      60
ctgaagagac tgagccagca cctgggcggc aaggtggagc tgtacgccaa gagagaggac   120
tgcaacagcg gcctggcctt cggcggcaac aagaccagaa gaatcgagtg ctgatccc     180
gacggcatcg agcagggctg cgactgcatc gtgagcatcg gcggcatcca gagccagaac   240
accagacagg gcgccgccgt gatggcccac ctgggcggca gtgcatcct ggtgcaggac    300
aactgggtga actacagcga cgccatctac gagagagcca tgaacatgga gatgagcaga   360
atcatgggcg ccgacgtgag actggacgcc gccgccttcg acctgggcat cagacccagc   420
tgggacaagg ccatgaccga gggcggcgag aacggcggca gacccttccc catccccgcc   480
gcctgcagcg accacccctt cggcggcctg ggctacgtgg ccttcgccga ggagatcaag   540
cagaacgacc acgacctggg cttcaagttc gactacatcg tggtgtgcag catcagcggc   600
agcaccaacg ccatgggcgc catggcctgg ccgccgaca tgagatgcaa gaacggcatc    660
ggcatcgacc tgtgcgccag acccgagcag accagaatga acatcctgca catcgtgaga   720
aagaccgccg acctggtgga cctgatgcac gagatctgcg aggacgacat catgatcgag   780
tgcagattcg cctaccccga gtacgccctg cccaacgacg gcaccctgga ggccatcaga   840
ctgtgcggca gcctggaggg cgtgctgacc gaccccgtgt acgagggcaa gagcatgcac   900
ggcatgatcg agatggtgag aagaggcgag ttccccgagg gcagcaaggt gctgtacgcc   960
cacctgggcg gcgcccccgc cctgaacgcc tacagcttcc tgttcagaaa cggc         1014
```

<210> SEQ ID NO 14
<211> LENGTH: 338
<212> TYPE: PRT
<213> ORGANISM: Artificial sequence
<220> FEATURE:
<223> OTHER INFORMATION: Amino acid sequence ACD, variant 10

<400> SEQUENCE: 14

```
Met Asn Val Gln Arg Tyr Asp Arg Tyr Pro Leu Ser Phe Leu Pro Ser
1               5                   10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
```

-continued

```
                35                  40                  45
Gly Asn Lys Thr Arg Arg Ile Glu Trp Leu Ile Pro Asp Gly Ile Glu
 50                  55                  60

Gln Gly Cys Asp Cys Ile Val Ser Ile Gly Gly Ile Gln Ser Gln Asn
 65                  70                  75                  80

Thr Arg Gln Gly Ala Ala Val Met Ala His Leu Gly Gly Lys Cys Ile
                 85                  90                  95

Leu Val Gln Asp Asn Trp Val Asn Tyr Ser Asp Ala Ile Tyr Glu Arg
                100                 105                 110

Ala Met Asn Met Glu Met Ser Arg Ile Met Gly Ala Asp Val Arg Leu
            115                 120                 125

Asp Ala Ala Phe Asp Leu Gly Ile Arg Pro Ser Trp Asp Lys Ala
130                 135                 140

Met Thr Glu Gly Gly Glu Asn Gly Gly Arg Pro Phe Pro Ile Pro Ala
145                 150                 155                 160

Ala Cys Ser Asp His Pro Phe Gly Gly Leu Gly Tyr Val Ala Phe Ala
                165                 170                 175

Glu Glu Ile Lys Gln Asn Asp His Asp Leu Gly Phe Lys Phe Asp Tyr
                180                 185                 190

Ile Val Val Cys Ser Ile Ser Gly Ser Thr Asn Ala Met Gly Ala Met
            195                 200                 205

Ala Trp Ala Ala Asp Met Arg Cys Lys Asn Gly Ile Gly Ile Asp Leu
210                 215                 220

Cys Ala Arg Pro Glu Gln Thr Arg Met Asn Ile Leu His Ile Val Arg
225                 230                 235                 240

Lys Thr Ala Asp Leu Val Asp Leu Met His Glu Ile Cys Glu Asp Asp
                245                 250                 255

Ile Met Ile Glu Cys Arg Phe Ala Tyr Pro Glu Tyr Ala Leu Pro Asn
                260                 265                 270

Asp Gly Thr Leu Glu Ala Ile Arg Leu Cys Gly Ser Leu Gly Gly Val
            275                 280                 285

Leu Thr Asp Pro Val Tyr Glu Gly Lys Ser Met His Gly Met Ile Glu
290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                325                 330                 335

Asn Gly
```

<210> SEQ ID NO 15
<211> LENGTH: 1014
<212> TYPE: DNA
<213> ORGANISM: Artificial sequence
<220> FEATURE:
<223> OTHER INFORMATION: Nucleotide sequence ACD, variant 11

<400> SEQUENCE: 15

```
atgcagctgc agagatggga gagataccccc gtgaccttcg ccccagccc catcaccccc      60 ctgaagagac tgagccagca cctgggcggc aaggtggagc tgtacgccaa gagagaggac     120
tgcaacagcg gcctggcctt cggcggcaac aagaccagaa agctggacta cctgatcccc     180
gacgccctgg acaacatgtg cgagaccgtg gtgagcatcc tgggcgccca gagcaaccag     240
accagacagg tggtggccgt ggtggcccac ctgggcatga gtgcgtgct ggtgcaggac     300 cagtggatga actggaccga cgccatctac gacagagtga tgaacatcga gatgaccaga     360
```

```
gtgatgggcc tggacgtgaa gctggacgcc gccctgttcg acatcggcat cagacccagc    420
tgggagaagg ccatgagcga ggtggtggag cagatcggca agcccttccc catcccctg     480 ggcagcagcg agagacccta cggcggcctg gctacgtgg ccttcgccga ggaggtgaga     540
aaccaggaca aggagctggc cttcagattc gagtacggcg ccatcagcag cgtgaccatg    600
accacccagg gcggcatggt gatcggcttc gccgccgacg gcagaagcaa gcaggtgctg    660
gtgatcgaca tgaccgtgaa gcccgagcag accaaggccc agatcctgag aatcgccaga    720
cacaccgccg aggccgtgga ggtgctgaga gacatctgcg acgaggacgt ggtgctggac    780
accaagttcg cctaccccga gtacggcgcc cccaacgacg gcaccggcga cgccatcaga    840
ctgtgcggca gcctggaggg cgtgctgacc gaccccgtgt acgagggcaa gagcatgcac    900
ggcatgatcg agatggtgag aagaggcgag ttccccgagg gcagcaaggt gctgtacgcc    960
cacctgggcg gcgcccccgc cctgaacgcc tacagcttcc tgttcagaaa cggc         1014
```

<210> SEQ ID NO 16
<211> LENGTH: 338
<212> TYPE: PRT
<213> ORGANISM: Artificial sequence
<220> FEATURE:
<223> OTHER INFORMATION: Amino acid sequence ACD, variant 11

<400> SEQUENCE: 16

```
Met Gln Leu Gln Arg Trp Glu Arg Tyr Pro Val Thr Phe Gly Pro Ser
1               5                   10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
        35                  40                  45

Gly Asn Lys Thr Arg Lys Leu Asp Tyr Leu Ile Pro Asp Ala Leu Asp
    50                  55                  60

Asn Met Cys Glu Thr Val Val Ser Ile Leu Gly Ala Gln Ser Asn Gln
65                  70                  75                  80

Thr Arg Gln Val Val Ala Val Ala His Leu Gly Met Lys Cys Val
                85                  90                  95

Leu Val Gln Asp Gln Trp Met Asn Trp Thr Asp Ala Ile Tyr Asp Arg
            100                 105                 110

Val Met Asn Ile Glu Met Thr Arg Val Met Gly Leu Asp Val Lys Leu
        115                 120                 125

Asp Ala Ala Leu Phe Asp Ile Gly Ile Arg Pro Ser Trp Glu Lys Ala
    130                 135                 140

Met Ser Glu Val Val Glu Gln Ile Gly Lys Pro Phe Pro Ile Pro Leu
145                 150                 155                 160

Gly Ser Ser Glu Arg Pro Tyr Gly Gly Leu Gly Tyr Val Ala Phe Ala
                165                 170                 175

Glu Glu Val Arg Asn Gln Asp Lys Glu Leu Ala Phe Arg Phe Glu Tyr
            180                 185                 190

Gly Ala Ile Ser Ser Val Thr Met Thr Thr Gln Gly Gly Met Val Ile
        195                 200                 205

Gly Phe Ala Ala Asp Gly Arg Ser Lys Gln Val Leu Val Ile Asp Met
    210                 215                 220

Thr Val Lys Pro Glu Gln Thr Lys Ala Gln Ile Leu Arg Ile Ala Arg
225                 230                 235                 240

His Thr Ala Glu Ala Val Glu Val Leu Arg Asp Ile Cys Asp Glu Asp
```

Val Val Leu Asp Thr Lys Phe Ala Tyr Pro Glu Tyr Gly Ala Pro Asn
                245                 250                 255
Asp Gly Thr Gly Asp Ala Ile Arg Leu Cys Gly Ser Leu Glu Gly Val
            260                 265                 270
Leu Thr Asp Pro Val Tyr Glu Gly Lys Ser Met His Gly Met Ile Glu
        275                 280                 285
Met Val Arg Arg Gly Glu Phe Pro Glu Gly Ser Lys Val Leu Tyr Ala
    290                 295                 300
His Leu Gly Gly Ala Pro Ala Leu Asn Ala Tyr Ser Phe Leu Phe Arg
305                 310                 315                 320
Asn Gly
                325                 330                 335

<210> SEQ ID NO 17
<211> LENGTH: 1014
<212> TYPE: DNA
<213> ORGANISM: Artificial sequence
<220> FEATURE:
<223> OTHER INFORMATION: Nucleotide sequence ACD, variant 12

<400> SEQUENCE: 17
atgaacctga acagatggga gagataccccc tgacctgggg cccccagccc catcaccccc      60
ctgaagagac tgagccagca cctgggcggc aaggtggagc tgtacgccaa gagagaggac     120
tgcaacagcg gcctggcctt cggcggcaac aagaccaaga agctggagtt cggcatcccc     180
gagggcatcg gcagggctg cgacaccctg gtgagcatcg gcggcatcca gagcaacaac     240
agcagacagg tggccgccgt ggccctgcac ctgggcatgc actgcgtgct gggcaacgag     300
aactgggtga acttcaccga ggccgtgtac gacaaggtgg gccagatcga catgagcaga     360
atcatgatcg ccgaggtgag actggacctg gccggcttcg acatcggcat cagacccagc     420
tgggacaagg gcatgagcga cgtgctggac cagggcggca agccctaccc catccccgtg     480
ggctgcagcg agcaccccta cgtgatgatc ggcttcgtgc tgtgggtgga ggaggtgaga     540
cagcaggaga aggacatcat gttcaagttc gacttcatcg tggtgtgcag cgtgaccggc     600
agcacccagg ccggcatggt ggtgggctac gccgccgacg gcagaaccaa gcagggcatg     660
ggcatcgacg ccagcgccaa gcccgaccag accaaggccc agatcgtgag aatcgccaga     720
cacaccgccg agctggtgga cctgctgaga gagatcaccg acgaggacgt gggcctggac     780
accagattcg cctaccccga gtacggcctg cccaacgaga tcaccctgga ggccatcaga     840
ctgtgcggca gcctggaggg cgtgctgacc gaccccgtgt acgagggcaa gagcatgcac     900
ggcatgatcg agatggtgag aagaggcgag ttccccgagg gcagcaaggt gctgtacgcc     960
cacctgggcg gcgcccccgc cctgaacgcc tacagcttcc tgttcagaaa cggc         1014

<210> SEQ ID NO 18
<211> LENGTH: 338
<212> TYPE: PRT
<213> ORGANISM: Artificial sequence
<220> FEATURE:
<223> OTHER INFORMATION: Amino acid sequence ACD, variant 12

<400> SEQUENCE: 18

Met Asn Leu Asn Arg Trp Glu Arg Tyr Pro Leu Thr Trp Ala Pro Ser
1               5                   10                  15
Pro Ile Thr Pro Leu Lys Arg Leu Ser Gln His Leu Gly Gly Lys Val
            20                  25                  30

```
Glu Leu Tyr Ala Lys Arg Glu Asp Cys Asn Ser Gly Leu Ala Phe Gly
         35                  40                  45

Gly Asn Lys Thr Lys Leu Glu Phe Gly Ile Pro Glu Gly Ile Glu
 50                  55                  60

Gln Gly Cys Asp Thr Leu Val Ser Ile Gly Ile Gln Ser Asn Asn
 65                  70                  75                  80

Ser Arg Gln Val Ala Val Ala Leu His Leu Gly Met His Cys Val
                 85                  90                  95

Leu Gly Asn Glu Asn Trp Val Asn Phe Thr Glu Ala Val Tyr Asp Lys
             100                 105                 110

Val Gly Gln Ile Asp Met Ser Arg Ile Met Ile Ala Glu Val Arg Leu
             115                 120                 125

Asp Leu Ala Gly Phe Asp Ile Gly Ile Arg Pro Ser Trp Asp Lys Gly
130                 135                 140

Met Ser Asp Val Leu Asp Gln Gly Gly Lys Pro Tyr Pro Ile Pro Val
145                 150                 155                 160

Gly Cys Ser Glu His Pro Tyr Val Met Ile Gly Phe Val Leu Trp Val
                165                 170                 175

Glu Glu Val Arg Gln Gln Glu Lys Asp Ile Met Phe Lys Phe Asp Phe
            180                 185                 190

Ile Val Val Cys Ser Val Thr Gly Ser Thr Gln Ala Gly Met Val Val
            195                 200                 205

Gly Tyr Ala Ala Asp Gly Arg Thr Lys Gln Gly Met Gly Ile Asp Ala
        210                 215                 220

Ser Ala Lys Pro Asp Gln Thr Lys Ala Gln Ile Val Arg Ile Ala Arg
225                 230                 235                 240

His Thr Ala Glu Leu Val Asp Leu Leu Arg Glu Ile Thr Asp Glu Asp
                245                 250                 255

Val Gly Leu Asp Thr Arg Phe Ala Tyr Pro Glu Tyr Gly Leu Pro Asn
            260                 265                 270

Glu Ile Thr Leu Glu Ala Ile Arg Leu Cys Gly Ser Leu Glu Gly Val
            275                 280                 285

Leu Thr Asp Pro Val Tyr Glu Gly Lys Ser Met His Gly Met Ile Glu
290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                325                 330                 335

Asn Gly

<210> SEQ ID NO 19
<211> LENGTH: 1014
<212> TYPE: DNA
<213> ORGANISM: Artificial sequence
<220> FEATURE:
<223> OTHER INFORMATION: Nucleotide sequence ACD, variant 13

<400> SEQUENCE: 19
atgaacctga acagattcga gaagtacccc ctgtgcttcg ccccagccc catcaccccc       60 ctgaagagac tgagccagca cctgggcggc aaggtggagc tgtacgccaa gagagaggac     120
tgcaacagcg gcctggcctt cggcggcaac aagaccagaa gactggagta cctgatcccc    180
gaggccatcg agcagatgtg cgacagcctg gtgagcatca tgggcatcca gagcaaccag    240
accagacagg tggccgccgt ggccgcccac ctgatgatga agtgcgtgct ggtgcaggag    300
```

```
cagtgggccc agtacagcga cgccgtgtac gacaaggtgg gcaacatcga gatgagcaga      360
atcatgggcg ccgacgtgag actggacgcc gccggcttcg acatcggcat cagacccagc      420
tgggagaaga tgatgagcga cgtgatggag cagggcggca agcccttccc catccccgcc      480
ggctgcagcg agcacccta cggcggcctg ggcttcgtgg gcttcgccga cgaggtgaga      540
cagcaggaga aggacctggg cttcaagttc gactacatcg tgatgtgcag cgtgaccggc      600
agcacccagg ccggcgtggt ggtgggcttc gccgccgacg gcagaagcaa gcaggtgatc      660
ggcatcgagg ccagcgccaa gcccgagcag accaagatcc agatcctgaa gatcgtgaga      720
cacaccgccg agctggtgga gctgatgaag gagctgagcg aggaggacgt ggtgctggac      780
accagatacg cctaccccga gtacgtgctg cccaacgagg gcagcgtgga ggccatcaga      840
ctgtgcggca gcctggaggg cgtgctgacc gaccccgtgt acgagggcaa gagcatgcac      900
ggcatgatcg agatggtgag aagaggcgag ttccccgagg gcagcaaggt gctgtacgcc      960
cacctgggcg gcgccccgc cctgaacgcc tacagcttcc tgttcagaaa cggc           1014
```

<210> SEQ ID NO 20
<211> LENGTH: 338
<212> TYPE: PRT
<213> ORGANISM: Artificial sequence
<220> FEATURE:
<223> OTHER INFORMATION: Amino acid sequence ACD, variant 13

<400> SEQUENCE: 20

```
Met Asn Leu Asn Arg Phe Glu Lys Tyr Pro Leu Cys Phe Gly Pro Ser
1               5                   10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
        35                  40                  45

Gly Asn Lys Thr Arg Arg Leu Glu Tyr Leu Ile Pro Glu Ala Ile Glu
    50                  55                  60

Gln Met Cys Asp Ser Leu Val Ser Ile Met Gly Ile Gln Ser Asn Gln
65                  70                  75                  80

Thr Arg Gln Val Ala Ala Val Ala Ala His Leu Met Met Lys Cys Val
                85                  90                  95

Leu Val Gln Glu Gln Trp Ala Gln Tyr Ser Asp Ala Val Tyr Asp Lys
            100                 105                 110

Val Gly Asn Ile Glu Met Ser Arg Ile Met Gly Ala Asp Val Arg Leu
        115                 120                 125

Asp Ala Ala Gly Phe Asp Ile Gly Ile Arg Pro Ser Trp Glu Lys Met
    130                 135                 140

Met Ser Asp Val Met Glu Gln Gly Gly Lys Pro Phe Pro Ile Pro Ala
145                 150                 155                 160

Gly Cys Ser Glu His Pro Tyr Gly Gly Leu Gly Phe Val Gly Phe Ala
                165                 170                 175

Asp Glu Val Arg Gln Gln Glu Lys Asp Leu Gly Phe Lys Phe Asp Tyr
            180                 185                 190

Ile Val Met Cys Ser Val Thr Gly Ser Thr Gln Ala Gly Val Val Val
        195                 200                 205

Gly Phe Ala Ala Asp Gly Arg Ser Lys Gln Val Ile Gly Ile Glu Ala
    210                 215                 220

Ser Ala Lys Pro Glu Gln Thr Lys Ile Gln Ile Leu Lys Ile Val Arg
225                 230                 235                 240
```

His Thr Ala Glu Leu Val Glu Leu Met Lys Glu Leu Ser Glu Glu Asp
            245                 250                 255

Val Val Leu Asp Thr Arg Tyr Ala Tyr Pro Glu Tyr Val Leu Pro Asn
        260                 265                 270

Glu Gly Ser Val Glu Ala Ile Arg Leu Cys Gly Ser Leu Gly Val
    275                 280                 285

Leu Thr Asp Pro Val Tyr Glu Gly Lys Ser Met His Gly Met Ile Glu
        290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
            325                 330                 335

Asn Gly

<210> SEQ ID NO 21
<211> LENGTH: 1014
<212> TYPE: DNA
<213> ORGANISM: Artificial sequence
<220> FEATURE:
<223> OTHER INFORMATION: Nucleotide sequence ACD, variant 14

<400> SEQUENCE: 21

```
atgaacctga acagattcga gagataccc ctgaccttcg gccccagccc catcacccc       60
ctgaagagac tgagccagca cctgggcggc aaggtggagc tgtacgccaa gagagaggac   120
tgcaacagcg gcctggcctt cggcggcaac aagagcagaa agatcgagta cctgatcccc   180
gaggccatcg gcagggctg cgactgcctg gtgagcatcg gcggcatcca gagcaaccag   240
tgcagacagg tggccgccgt ggccgcccac ctgctgatga gagcgtgct ggtgcaggag   300
aactacatga actacagcga ggccgtgtgg gacagagtgg gcaacatcga gatgagcaga   360
atcatgggcg ccgacgtgag actggacgcc gccggcttcg acatcggcat cagacccagc   420
tgggagaagg ccatgaccga cgtgatggag cagggcggca gacccttccc catccccggc   480
ggctgcagcg agcacccta cggcgtgctg gctgggtgg gcttcgccga ggaggtgaga   540
cagcaggaga aggagctggg cttcaagttc gagtacatcg tggtgtgcag cgtgaccggc   600
agcacccagg ccgccatggt ggtgggcttc gccgccgacg cagaagcaa gaacgtgatc   660
ggcatcgacg ccagcgccag acccgagcag accaaggccc agctgctgag aatcgccaga   720
cacagcgccg agctggtgga gctggtgaga gagatcaccg aggaggacat cctggccgac   780
accagattcg tgtaccccga gtacctgctg cccaacgagg gcaccctgga ggccatcaga   840
ctgtgcggca gcctggaggg cgtgctgacc gaccccgtgt acgagggcaa gagcatgcac   900
ggcatgatcg agatggtgag aagaggcgag ttccccgagg gcagcaaggt gctgtacgcc   960
cacctgggcg gcgcccccgc cctgaacgcc tacagcttcc tgttcagaaa cggc       1014
```

<210> SEQ ID NO 22
<211> LENGTH: 338
<212> TYPE: PRT
<213> ORGANISM: Artificial sequence
<220> FEATURE:
<223> OTHER INFORMATION: Amino acid sequence ACD, variant 14

<400> SEQUENCE: 22

Met Asn Leu Asn Arg Phe Glu Arg Tyr Pro Leu Thr Phe Gly Pro Ser
1               5                   10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
            35                  40                  45

Gly Asn Lys Ser Arg Lys Ile Glu Tyr Leu Ile Pro Glu Ala Ile Glu
        50                  55                  60

Gln Gly Cys Asp Cys Leu Val Ser Ile Gly Ile Gln Ser Asn Gln
65                  70                  75                  80

Cys Arg Gln Val Ala Val Ala Ala His Leu Leu Met Lys Ser Val
                85                  90                  95

Leu Val Gln Glu Asn Tyr Met Asn Tyr Ser Glu Ala Val Trp Asp Arg
            100                 105                 110

Val Gly Asn Ile Glu Met Ser Arg Ile Met Gly Ala Asp Val Arg Leu
        115                 120                 125

Asp Ala Ala Gly Phe Asp Ile Gly Ile Arg Pro Ser Trp Glu Lys Ala
130                 135                 140

Met Thr Asp Val Met Glu Gln Gly Gly Arg Pro Phe Pro Ile Pro Gly
145                 150                 155                 160

Gly Cys Ser Glu His Pro Tyr Gly Val Leu Gly Trp Val Gly Phe Ala
                165                 170                 175

Glu Glu Val Arg Gln Gln Glu Lys Glu Leu Gly Phe Lys Phe Glu Tyr
            180                 185                 190

Ile Val Val Cys Ser Val Thr Gly Ser Thr Gln Ala Ala Met Val Val
        195                 200                 205

Gly Phe Ala Ala Asp Gly Arg Ser Lys Asn Val Ile Gly Ile Asp Ala
    210                 215                 220

Ser Ala Arg Pro Glu Gln Thr Lys Ala Gln Leu Leu Arg Ile Ala Arg
225                 230                 235                 240

His Ser Ala Glu Leu Val Glu Leu Val Arg Glu Ile Thr Glu Glu Asp
                245                 250                 255

Ile Leu Ala Asp Thr Arg Phe Val Tyr Pro Glu Tyr Leu Leu Pro Asn
            260                 265                 270

Glu Gly Thr Leu Glu Ala Ile Arg Leu Cys Gly Ser Leu Glu Gly Val
        275                 280                 285

Leu Thr Asp Pro Val Tyr Glu Gly Lys Ser Met His Gly Met Ile Glu
    290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                325                 330                 335

Asn Gly

<210> SEQ ID NO 23
<211> LENGTH: 1014
<212> TYPE: DNA
<213> ORGANISM: Artificial sequence
<220> FEATURE:
<223> OTHER INFORMATION: Nucleotide sequence ACD, variant 15

<400> SEQUENCE: 23
atgcagctga acagatacga gagatacccc ctgaccttcg ccccagccc catcaccccc      60 ctgaagagac tgagccagca cctgggcggc aaggtggagc tgtacgccaa gagagaggac     120
tgcaacagcg gcctggcctt cggcggcaac aagaccagac acctggagta cctgatcccc     180
gaggccggcg agcagggctg cgacaccctg gtgagcatcg gcggcatcca gagcaaccag     240
accagacagg tggccgccgt ggccgcccac ctgggcatga agtgcgtgct ggtgcaggag     300

```
aactgggtga actacagcga cgccgtgtac gacaaggtgg gcaacatcga gatgagcaga      360
atcatgggcg ccgacgtgag actggacgcc gccggcttcg acatcggcat cagacccagc      420
tgggagagag ccatgagcga cgtggtggag cagggcggca agcccttccc cgtgcccgcc      480
ggctgcagcg agcaccccta cggcggcatg ggcttcgtgg gcttcgccga ggaggtgaga      540
cagcaggaga aggagctggg cttcaagttc gactacgccg tggtgtgcag cgtgaccggc      600
agcacccagg ccggcatggt ggtgggcttc gccgccgacg gcagaagcaa gaacgtgatc      660
ggcatcgacg ccagcgccaa gcccgagcag accagagccc agatcgtgag aatcgccaga      720
cacaccgccg acctggtgga gctgggcaga gagatcaccg aggaggacgt ggtgctggac      780
tgcagattcg cctaccccga gtacggcctg cccaacgagg gcaccctgga ggccatcaga      840
ctgtgcggca gcctggaggg cgtgctgacc gaccccgtgt acgagggcaa gagcatgcac      900
ggcatgatcg agatggtgag aagaggcgag ttccccgagg gcagcaaggt gctgtacgcc      960
cacctgggcg gcgcccccgc cctgaacgcc tacagcttcc tgttcagaaa cggc           1014
```

<210> SEQ ID NO 24
<211> LENGTH: 338
<212> TYPE: PRT
<213> ORGANISM: Artificial sequence
<220> FEATURE:
<223> OTHER INFORMATION: Amino acid sequence ACD, variant 15

<400> SEQUENCE: 24

```
Met Gln Leu Asn Arg Tyr Glu Arg Tyr Pro Leu Thr Phe Ala Pro Ser
1               5                   10                  15

Pro Ile Thr Pro Leu Lys Arg Leu Ser Gln His Leu Gly Gly Lys Val
            20                  25                  30

Glu Leu Tyr Ala Lys Arg Glu Asp Cys Asn Ser Gly Leu Ala Phe Gly
        35                  40                  45

Gly Asn Lys Thr Arg His Leu Glu Tyr Leu Ile Pro Glu Ala Gly Glu
    50                  55                  60

Gln Gly Cys Asp Thr Leu Val Ser Ile Gly Gly Ile Gln Ser Asn Gln
65                  70                  75                  80

Thr Arg Gln Val Ala Ala Val Ala Ala His Leu Gly Met Lys Cys Val
                85                  90                  95

Leu Val Gln Glu Asn Trp Val Asn Tyr Ser Asp Ala Val Tyr Asp Lys
            100                 105                 110

Val Gly Asn Ile Glu Met Ser Arg Ile Met Gly Ala Asp Val Arg Leu
        115                 120                 125

Asp Ala Ala Gly Phe Asp Ile Gly Ile Arg Pro Ser Trp Glu Arg Ala
    130                 135                 140

Met Ser Asp Val Val Glu Gln Gly Gly Lys Pro Phe Pro Val Pro Ala
145                 150                 155                 160

Gly Cys Ser Glu His Pro Tyr Gly Gly Met Gly Phe Val Gly Phe Ala
                165                 170                 175

Glu Glu Val Arg Gln Gln Glu Lys Glu Leu Gly Phe Lys Phe Asp Tyr
            180                 185                 190

Ala Val Val Cys Ser Val Thr Gly Ser Thr Gln Ala Gly Met Val Val
        195                 200                 205

Gly Phe Ala Ala Asp Gly Arg Ser Lys Asn Val Ile Gly Ile Asp Ala
    210                 215                 220

Ser Ala Lys Pro Glu Gln Thr Arg Ala Gln Ile Val Arg Ile Ala Arg
225                 230                 235                 240
```

His Thr Ala Asp Leu Val Glu Leu Gly Arg Glu Ile Thr Glu Glu Asp
            245                 250                 255

Val Val Leu Asp Cys Arg Phe Ala Tyr Pro Glu Tyr Gly Leu Pro Asn
        260                 265                 270

Glu Gly Thr Leu Glu Ala Ile Arg Leu Cys Gly Ser Leu Glu Gly Val
    275                 280                 285

Leu Thr Asp Pro Val Tyr Glu Gly Lys Ser Met His Gly Met Ile Glu
    290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
            325                 330                 335

Asn Gly

<210> SEQ ID NO 25
<211> LENGTH: 1014
<212> TYPE: DNA
<213> ORGANISM: Artificial sequence
<220> FEATURE:
<223> OTHER INFORMATION: Nucleotide sequence ACD, variant 16

<400> SEQUENCE: 25
atgaacctga acagattcga gatacccc ctgaccttcg ccccagccc catcacccc      60 ctgaagagac tgagccagca cctgggcggc aaggtggagc tgtacgccaa gagagaggac    120
tgcaacagcg gcctggcctt cggcggcaac aagaccagaa agctggagta cctgatcccc    180
gaggccatcg agcagggctg cgacaccctg gtgagcatcg gcggcatcca gagcaaccag    240
accagaaacg tggccgccgt ggccgcccac ctgggcatga agtgcgtgct ggtgcaggag    300
aactgggtgc agtacagcga cgccgtgttc gacagagtgg gcaacatcga gatgagcaga    360
atcatgggcg ccgaggtgag actggacgcc gccggcttcg acatcggcat cagacccagc    420
tgggagaagg ccatgagcga cgtggtggag cagggcggca agcccttccc catccccgcc    480
ggctgcagcg agcacccta cggcggcctg ggcttcgtgg gcttcgccga ggaggccaga    540
cagcaggaga aggaggtgat cttcaagttc gactacatcg tggtgtgcag cgtgaccggc    600
agcacccagg ccggcatggt ggtgggcttc gccgccgacg gcagaagcaa gaacgtgatc    660
ggcatcgacc cagcgccaa gcccgagcag accaaggccc agatcctgag aatcgccaga    720
cacaccgccg agctggtgga gctgggccac gagatcaccg aggaggacgt ggtgctggac    780
agcagattcg cctaccccga gtacggcctg cccaacgagg gcaccggcga ggccggcaga    840
ctgtgcggca gcctggaggg cgtgctgacc gaccccgtgt acgagggcaa gagcatgcac    900
ggcatgatcg agatggtgag aagaggcgag ttccccgagg gcagcaaggt gctgtacgcc    960
cacctgggcg gcgcccccgc cctgaacgcc tacagcttcc tgttcagaaa cggc         1014

<210> SEQ ID NO 26
<211> LENGTH: 338
<212> TYPE: PRT
<213> ORGANISM: Artificial sequence
<220> FEATURE:
<223> OTHER INFORMATION: Amino acid sequence ACD, variant 16

<400> SEQUENCE: 26

Met Asn Leu Asn Arg Phe Glu Arg Tyr Pro Leu Thr Phe Gly Pro Ser
1               5                   10                  15

Pro Ile Thr Pro Leu Lys Arg Leu Ser Gln His Leu Gly Gly Lys Val

```
                          20                      25                      30
Glu Leu Tyr Ala Lys Arg Glu Asp Cys Asn Ser Gly Leu Ala Phe Gly
             35                      40                      45

Gly Asn Lys Thr Arg Lys Leu Glu Tyr Leu Ile Pro Glu Ala Ile Glu
     50                      55                      60

Gln Gly Cys Asp Thr Leu Val Ser Ile Gly Ile Gln Ser Asn Gln
 65                      70                      75                      80

Thr Arg Asn Val Ala Ala Val Ala Ala His Leu Gly Met Lys Cys Val
                     85                      90                      95

Leu Val Gln Glu Asn Trp Val Gln Tyr Ser Asp Ala Val Phe Asp Arg
                100                     105                     110

Val Gly Asn Ile Glu Met Ser Arg Ile Met Gly Ala Glu Val Arg Leu
                115                     120                     125

Asp Ala Ala Gly Phe Asp Ile Gly Ile Arg Pro Ser Trp Glu Lys Ala
        130                     135                     140

Met Ser Asp Val Val Glu Gln Gly Gly Lys Pro Phe Pro Ile Pro Ala
145                     150                     155                     160

Gly Cys Ser Glu His Pro Tyr Gly Gly Leu Gly Phe Val Gly Phe Ala
                    165                     170                     175

Glu Glu Ala Arg Gln Gln Glu Lys Glu Val Ile Phe Lys Phe Asp Tyr
                180                     185                     190

Ile Val Val Cys Ser Val Thr Gly Ser Thr Gln Ala Gly Met Val Val
                195                     200                     205

Gly Phe Ala Ala Asp Gly Arg Ser Lys Asn Val Ile Gly Ile Asp Ala
        210                     215                     220

Ser Ala Lys Pro Glu Gln Thr Lys Ala Gln Ile Leu Arg Ile Ala Arg
225                     230                     235                     240

His Thr Ala Glu Leu Val Glu Leu Gly His Glu Ile Thr Glu Glu Asp
                    245                     250                     255

Val Val Leu Asp Ser Arg Phe Ala Tyr Pro Glu Tyr Gly Leu Pro Asn
                260                     265                     270

Glu Gly Thr Gly Glu Ala Gly Arg Leu Cys Gly Ser Leu Glu Gly Val
            275                     280                     285

Leu Thr Asp Pro Val Tyr Glu Gly Lys Ser Met His Gly Met Ile Glu
        290                     295                     300

Met Val Arg Arg Gly Glu Phe Pro Glu Gly Ser Lys Val Leu Tyr Ala
305                     310                     315                     320

His Leu Gly Gly Ala Pro Ala Leu Asn Ala Tyr Ser Phe Leu Phe Arg
                    325                     330                     335

Asn Gly
```

FUNGAL RESISTANT PLANTS EXPRESSING ACD

This application is a continuation of Ser. No. 14/390,505, which is a U.S. National Stage application of International Application No. PCT/EP2013/055347, filed Mar. 15, 2013, which claims the benefit of U.S. Provisional Application No. 61/620,452, filed Apr. 5, 2012, and also claims priority under 35 U.S.C. § 119 to European Patent Application No. 12163265.7, filed Apr. 5, 2012; the entire contents of these applications are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "73495A_Seqlisting.txt" created on Jun. 5, 2017, and is 51,960 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of a ACD protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding a ACD protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as many rusts, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, six dominant genes Rpp1-5 and Rpp?(Hyuuga), which mediate resistance of soy to *P. pachyrhizi*, were discovered. The resistance was lost rapidly, as *P. pychyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust.

Surprisingly, we found that fungal pathogens, in particular rust pathogens (i.e., fungal pathogens of the order Pucciniales), preferably fungal pathogens of the family Phacopsoraceae, for example soybean rust, can be controlled by overexpression of the ethylene precoursor degrading enzyme aminocyclopropane carboxylic acid deaminase (ACD). Thus, without being limited by theory, we found that fungal resistance can be achieved by inhibition of the ethylene signaling pathway, at least by overexpression of an ACD gene, in a plant, plant part, and/or plant cell.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, in transgenic plants, transgenic plant parts, or transgenic plant cells by overexpressing one or more ACD nucleic acids.

A further object is to provide transgenic plants resistant against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous ACD nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The terms "inhibition of the ethylene signaling pathway", "reduction of the ethylene signaling pathway", or "suppression of the ethylene pathway" or "inactivation of the ethylene pathway" means that the ethylene signaling pathway, e.g., as shown in FIG. 1, in a plant, plant part, or plant cell is disturbed as compared to a wildtype plant, plant part, or plant cell. Preferably, the disturbance of the ethylene signaling pathway leads to a reduced rate of ethylene production, a loss of ethylene production or a lowered ethylene content as compared to a wildtype plant, plant part, or plant cell exposed to the same conditions. Furthermore, the ethylene signaling pathway can be disturbed by altering the activity of one or more ethylene signaling compounds with or without effecting the ethylene production or ethylene content.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of nucleic acid with other nucleic acids, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* (Sydow) and *Phakopsora meibomiae* (Arthur)—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous ACD nucleic acid, functional fragments thereof and/or an exogenous nucleic acid capable of hybridizing with an ACD nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% \text{ G}+\text{C})$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole ACD nucleic acids. Preferably, the complementary polynucleotide hybridizes with parts of the ACD nucleic acids capable to provide soybean rust resistance by overexpression or downregulation, respectively.

"Identity" or "homology" or "similarity" between two nucleic acids sequences or amino acid sequences refers in each case over the entire length of the ACD nucleic acid sequences or ACD amino acid sequences. The terms "identity", "homology" and "similarity" are used herein interchangeably.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:
Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the ACD nucleic acids or ACD proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous ACD nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous ACD nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more ACD nucleic acids, all those constructions brought about by man by gentechnological methods in which either (a) the sequences of the ACD nucleic acids or a part thereof, or (b) genetic control sequence(s) which is operably linked with the ACD nucleic acid sequence according to the invention, for example a promoter, or (c) a) and b)

are not located in their natural genetic environment or have been modified by man by gentechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid may also refer to a nucleic acid in an isolated form. A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

It shall further be noted that in the context of the present invention, the term "isolated nucleic acid" or "isolated protein" may in some instances be considered as a synonym for a "recombinant nucleic acid" or a "recombinant protein", respectively and refers to a nucleic acid or protein that is not located in its natural genetic environment and/or that has been modified by genetechnical methods. The isolated gene may be isolated from an organism or may be manmade, for example by chemical synthesis.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous ACD nucleic acid, recombinant construct, vector or expression cassette including one or more ACD nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous ACD nucleic acid or exogenous ACD protein.

Natural locus means the location on a specific chromosome, preferably the location between certain genes, more preferably the same sequence background as in the original plant which is transformed.

Preferably, the transgenic plant, plant cell or tissue thereof expresses the ACD nucleic acids, ACD constructs or ACD expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the ACD nucleic acids has an identity as defined above over a length of at least 20%, at least 30%, at least 50%, at least 75%, at least 90% of the nucleotides of the respective ACD nucleic acid.

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the ACD nucleotide sequence as defined by SEQ ID NO: 1 or the ACD protein sequence as defined by SEQ ID NO: 2.

The term "increased activity" or "enhanced activity" as used herein means any protein having increased activity and which provides an increased fungal resistance compared with the wildtype plant merely expressing the respective endogenous ACD nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

The ACD nucleic acid to be overexpressed in order to achieve increased resistance to fungal pathogens, e.g., of the family Phacopsoraceae, for example soybean rust, is preferably a nucleic acid coding for an aminocyclopropane carboxylic acid deaminase (ACD) protein, and is preferably as defined by SEQ ID NO: 1, 3-10, 11, 13, 15, 17, 19, 21, 23, or 25, or a fragment, homolog, derivative, orthologue or paralogue thereof. Preferably, the nucleic acid coding for an aminocyclopropane carboxylic acid deaminase (ACD) protein of the present invention has at least 60% identity, preferably at least 70% sequence identity, at least 80%, at least 90%, at least 95%, at least 98%, at least 99% sequence identity, or even 100% sequence identity with SEQ ID NO: 1, 3-10, 11, 13, 15, 17, 19, 21, 23, or 25 or is a functional fragment thereof. Most preferred is at least 95% identity, more preferred is at least 98% or at least 99% identity. Percentages of identity of a nucleic acid are indicated with reference to the entire nucleotide region given in a sequence specifically disclosed herein. Preferably, the ACD nucleic acid comprises at least about 100, at least about 200, at least about 300, at least about 400, at least about 500, at least about 600, at least about 700, at least about 800, at least about 850, at least about 900, at least about 950, at least about 975, at least about 990, at least about 1000, or at least about 1010 nucleotides, preferably continuous nucleotides, preferably counted from the 5' or 3' end of the nucleic acid or up to the full length of the nucleic acid sequence set out in SEQ ID NO: 1, 3-10, 11, 13, 15, 17, 19, 21, 23, or 25.

Preferably, the nucleic acid coding for an aminocyclopropane carboxylic acid deaminase (ACD) protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof. Most preferred is at least 95% identity, more preferred is at least 98% or at least 99% identity. Percentages of identity of a nucleic acid are indicated with reference to the entire nucleotide region given in a sequence specifically disclosed herein. Preferably, the ACD nucleic acid comprises at least about 100, at least about 200, at least about 300, at least about 400, at least about 500, at least about 600, at least about 700, at least about 800, at least about 850, at least about 900, at least about 950, at least about 975, at least about 990, at least about 1000, or at least about 1010 nucleotides, preferably continuous nucleotides, preferably counted from the 5' or 3' end of the nucleic acid or up to the full length of the nucleic acid sequence set out in SEQ ID NO: 1.

The ACD protein preferably is a 1-aminocyclopropane-1-carboxylic acid deaminase, and preferably defined by SEQ ID NO: 2, 12, 14, 16, 18, 20, 22, 24, or 26, or a fragment, homolog, derivative, orthologue or paralogue thereof. Preferably, the ACD protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 1, 3-10, 11, 13, 15, 17, 19, 21, 23, or 25 or a functional fragment thereof. More preferably, the ACD protein of the present invention has at least 60%, preferably at least 70% sequence identity, at least 80%, at least 90%, at least 95%, at least 98%, at least 99% sequence identity, or even 100% sequence identity with SEQ ID NO: 2, 12, 14, 16, 18, 20, 22, 24, or 26, or is a functional fragment thereof, an orthologue or a paralogue thereof. Most preferred is at least 95% identity, more preferred is at least 98% or at least 99% identity. Percentages of identity of a polypeptide or protein are indicated with reference to the entire amino acid sequence specifically disclosed herein. Preferably, the ACD protein comprises at least about 50, at least about 75, at least about 100, at least about 125, at least about 150, at least about 175, at least about 200, at least about 225, at least about 250, at least about 275, at least about 300, at least about 310, at least about 320, at least about 325, at least about 330 or at least about 335 amino acid residues, preferably continuous amino acid residues, preferably counted from the N-terminus or the C-terminus of the amino acid sequence, or up to the full length of the amino acid sequence set out in SEQ ID NO: 2, 12, 14, 16, 18, 20, 22, 24, or 26.

The ACD protein preferably is a 1-aminocyclopropane-1-carboxylic acid deaminase, and preferably defined by SEQ ID NO: 2, or a fragment, homolog, derivative, orthologue or paralogue thereof. Preferably, the ACD protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof. More preferably, the ACD protein of the present invention has at least 60%, preferably at least 70% sequence identity, at least 80%, at least 90%, at least 95%, at least 98%, at least 99% sequence identity, or even 100% sequence identity with SEQ ID NO: 2, or is a functional fragment thereof, an orthologue or a paralogue thereof. Most preferred is at least 95% identity, more preferred is at least 98% or at least 99% identity. Percentages of identity of a polypeptide or protein are indicated with reference to the entire amino acid sequence specifically disclosed herein. Preferably, the ACD protein comprises at least about 50, at least about 75, at least about 100, at least about 125, at least about 150, at least about 175, at least about 200, at least about 225, at least about 250, at least about 275, at least about 300, at least about 310, at least about 320, at least about 325, at least about 330 or at least about 335 amino acid residues, preferably continuous amino acid residues, preferably counted from the N-terminus or the C-terminus of the amino acid sequence, or up to the full length of the amino acid sequence set out in SEQ ID NO: 2.

One embodiment of the invention is a method for increasing fungal resistance, preferably resistance to Phacopsoracea, for example soy bean rust, in a plant, plant part, or plant cell by increasing the expression of a ACD protein or a functional fragment, orthologue, paralogue or homologue thereof in comparison to wild-type plants, wild-type plant parts or wild-type plant cells.

The present invention also provides a method for increasing resistance to fungal pathogens, in particular fungal pathogens of the family Phacopsoraceae, preferably against fungal pathogens of the genus *Phacopsora*, most preferably against *Phakopsora pachyrhizi* (Sydow) and *Phakopsora meibomiae* (Arthur), also known as soy bean rust in plants or plant cells, wherein in comparison to wild type plants, wild type plant parts, or wild type plant cells a ACD protein is overexpressed.

The present invention further provides a method for increasing resistance to fungal pathogens of the genus *Phacopsora*, most preferably against *Phakopsora pachyrhizi* (Sydow) and *Phakopsora meibomiae* (Arthur), also known as soy bean rust in plants or plant cells by overexpression of a ACD protein.

In preferred embodiments, the protein amount and/or function of the ACD protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the ACD nucleic acid.

In one embodiment of the invention, the ACD protein is encoded by (i) a nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 3-10, 11, 13, 15, 17, 19, 21, 23, or 25, a functional fragment thereof, or an orthologue or a paralogue thereof; or by (ii) a nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 12, 14, 16, 18, 20, 22, 24, or 26, a functional fragment thereof, an orthologue or a paralogue thereof, preferably the ACD nucleic acid encodes a ACD protein that has essentially the same biological activity as an ACD protein encoded by SEQ ID NO: 2; preferably the encoded ACD protein confers enhanced fungal resistance relative to control plants;

(iii) a nucleic acid capable of hybridizing under stringent conditions with any of the nucleic acids according to (i) or (ii) or a complementary sequence (complement) thereof, and which preferably encodes a ACD protein that has essentially the same biological activity as an ACD protein encoded by SEQ ID NO: 2; preferably the encoded ACD protein confers enhanced fungal resistance relative to control plants; or by (iv) a nucleic acid encoding the same ACD protein as the ACD nucleic acids of (i) to (iii) above, but differing from the ACD nucleic acids of (i) to (iii) above due to the degeneracy of the genetic code.

In one embodiment of the invention, the ACD protein is encoded by (i) a nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, a functional fragment thereof, or an orthologue or a paralogue thereof; preferably the ACD protein that has essentially the same biological activity as an ACD protein encoded by SEQ ID NO: 2; preferably the ACD protein confers enhanced fungal resistance relative to control plants;
or by (ii) a nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, a functional fragment thereof, an orthologue or a paralogue thereof, preferably the nucleic acid encodes a ACD protein that has essentially the same biological activity as an ACD protein encoded by SEQ ID NO: 2; preferably the encoded ACD protein confers enhanced fungal resistance relative to control plants;

(iii) a nucleic acid capable of hybridizing under stringent conditions with any of the nucleic acids according to (i) or (ii) or a complementary sequence (complement) thereof, and which preferably encodes a ACD protein that has essentially the same biological activity as an ACD protein encoded by SEQ ID NO: 2; preferably the encoded ACD protein confers enhanced fungal resistance relative to control plants; or by (iv) a nucleic acid encoding the same ACD protein as the ACD nucleic acids of (i) to (iii) above, but differing from the ACD nucleic acids of (i) to (iii) above due to the degeneracy of the genetic code.

Another preferred embodiment is a method for increasing fungal resistance, preferably resistance to Phacopsoracea, for example soy bean rust, in a plant, plant part, or plant cell, by increasing the expression of a ACD protein or a functional fragment, orthologue, paralogue or homologue thereof wherein the ACD protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1, 3-10, 11, 13, 15, 17, 19, 21, 23, or 25 or a functional fragment thereof, an orthologue or a paralogue thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, 12, 14, 16, 18, 20, 22, 24, or 26; preferably the encoded ACD protein confers enhanced fungal resistance relative to control plants; and/or by (iii) an exogenous nucleic acid capable of hybridizing under stringent conditions with any of the nucleic acids according to (i) or (ii) or a complement thereof is a further embodiment of the invention, and which preferably encodes a ACD protein that has essentially the same biological activity as an ACD protein encoded by SEQ ID NO: 2, 12, 14, 16, 18, 20, 22, 24, or 26; preferably the encoded ACD protein confers enhanced fungal resistance relative to control plants; and/or by (iv) an exogenous nucleic acid encoding the same ACD protein as the ACD nucleic acids of (i) to (iii) above, but differing from the ACD nucleic acids of (i) to (iii) above due to the degeneracy of the genetic code.

Another preferred embodiment is a method for increasing fungal resistance, preferably resistance to Phacopsoracea, for example soy bean rust, in a plant, plant part, or plant cell, by increasing the expression of a ACD protein or a functional fragment, orthologue, paralogue or homologue thereof wherein the ACD protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof;

(iii) an exogenous nucleic acid capable of hybridizing under stringent conditions with any of the nucleic acids according to (i) or (ii) or a complement thereof is a further embodiment of the invention, and which preferably encodes a ACD protein that has essentially the same biological activity as an ACD protein encoded by SEQ ID NO: 2; preferably the encoded ACD protein confers enhanced fungal resistance relative to control plants; and/or by (iv) an exogenous nucleic acid encoding the same ACD protein as the ACD nucleic acids of (i) to (iii) above, but differing from the ACD nucleic acids of (i) to (iii) above due to the degeneracy of the genetic code.

In a further method of the invention, the method comprises the steps of (a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 3-10, 11, 13, 15, 17, 19, 21, 23, or 25 or a functional fragment thereof, or an orthologue or a paralogue thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 12, 14, 16, 18, 20, 22, 24, or 26, a functional fragment thereof, an orthologue or a paralogue thereof;
   (iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
   (iv) a nucleic acid encoding the same ACD protein as the ACD nucleic acids of (i) to (iii) above, but differing from the ACD nucleic acids of (i) to (iii) above due to the degeneracy of the genetic code;
in functional linkage with a promoter;
(b) regenerating the plant from the plant cell; and
(c) expressing said nucleic acid, optionally wherein the nucleic acid which codes for a ACD protein is expressed in an amount and for a period sufficient to generate or to increase soybean rust resistance in said plant.

In a further method of the invention, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, or an orthologue or a paralogue thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof;
   (iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
   (iv) a nucleic acid encoding the same ACD protein as the ACD nucleic acids of (i) to (iii) above, but differing from the ACD nucleic acids of (i) to (iii) above due to the degeneracy of the genetic code;
in functional linkage with a promoter;
(b) regenerating the plant from the plant cell; and
(c) expressing said nucleic acid, optionally wherein the nucleic acid which codes for a ACD protein is expressed in an amount and for a period sufficient to generate or to increase soybean rust resistance in said plant.

A preferred embodiment is a method for increasing resistance to soy bean rust in a soy bean plant, soy bean plant part, or soy bean plant cell, by increasing the expression of a ACD protein, wherein the ACD protein is encoded by
(i) an exogenous nucleic acid having at least 95%, at least 98%, at least 99% sequence identity, or even 100% sequence identity with SEQ ID NO: 1, 3-10, 11, 13, 15, 17, 19, 21, 23, or 25;
(ii) an exogenous nucleic acid encoding a protein having at least 95%, at least 98%, at least 99% sequence identity, or even 100% sequence identity with SEQ ID NO: 2, 12, 14, 16, 18, 20, 22, 24, or 26;
(iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
(iv) an exogenous nucleic acid encoding the same ACD protein as the ACD nucleic acids of (i) to (iii) above, but differing from the ACD nucleic acids of (i) to (iii) above due to the degeneracy of the genetic code;
wherein increasing the expression of the ACD protein is achieved by transforming the soy bean plant, plant part or plant cell with a nucleic acid comprising the nucleic acid set out under item (i) or (ii) or (iii).

A preferred embodiment is a method for increasing resistance to soy bean rust in a soy bean plant, soy bean plant part, or soy bean plant cell, by increasing the expression of a ACD protein, wherein the ACD protein is encoded by
(i) an exogenous nucleic acid having at least 95%, at least 98%, at least 99% sequence identity, or even 100% sequence identity with SEQ ID NO: 1;
(ii) an exogenous nucleic acid encoding a protein having at least 95%, at least 98%, at least 99% sequence identity, or even 100% sequence identity with SEQ ID NO: 2;
(iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
(iv) an exogenous nucleic acid encoding the same ACD protein as the ACD nucleic acids of (i) to (iii) above, but differing from the ACD nucleic acids of (i) to (iii) above due to the degeneracy of the genetic code;
wherein increasing the expression of the ACD protein is achieved by transforming the soy bean plant, plant part or plant cell with a nucleic acid comprising the nucleic acid set out under item (i) or (ii) or (iii).

Also a preferred embodiment is a method for increasing resistance to soy bean rust in a soy bean plant, soy bean plant part, or soy bean plant cell, by increasing the expression of a ACD protein, wherein the ACD protein is encoded by
(i) an exogenous nucleic acid having at least 95%, at least 98%, at least 99% sequence identity, or even 100% sequence identity with SEQ ID NO: 1; or
(ii) an exogenous nucleic acid encoding a protein having at least 95%, at least 98%, at least 99% sequence identity, or even 100% sequence identity with SEQ ID NO: 2;
wherein increasing the expression of the ACD protein is achieved by transforming the soy bean plant, plant part or plant cell with a nucleic acid comprising the nucleic acid set out under item (i) or (ii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
| --- | --- |
| Leaf rust | Puccinia recondita |
| Yellow rust | P. striiformis |
| Powdery mildew | Erysiphe graminis/Blumeria graminis |
| Rust (common corn) | Puccinia sorghi |
| Rust (Southern corn) | Puccinia polysora |
| Tobacco leaf spot | Cercospora nicotianae |
| Rust (soybean) | Phakopsora pachyrhizi, P. meibomiae |
| Rust (tropical corn) | Physopella pallescens, P. zeae = Angiopsora zeae |

TABLE 3

Diseases caused by necrotrophic and/or hemibiotrophic fungi and Oomycetes

| Disease | Pathogen |
| --- | --- |
| Plume blotch | Septoria (Stagonospora) nodorum |
| Leaf blotch | Septoria tritici |
| Ear fusarioses | Fusarium spp. |
| Late blight | Phytophthora infestans |
| Anthrocnose leaf blight | Colletotrichum graminicola (teleomorph: |
| Anthracnose stalk rot | Glomerella graminicola Politis); Glomerella tucumanensis (anamorph: Glomerella falcatum Went) |
| Curvularia leaf spot | Curvularia clavata, C. eragrostidis, = C. maculans (teleomorph: Cochliobolus eragrostidis), Curvularia inaequalis, C. intermedia (teleomorph: Cochliobolus intermedius), Curvularia lunata (teleomorph: Cochliobolus lunatus), Curvularia pallescens (teleomorph: Cochliobolus pallescens), Curvularia senegalensis, C. tuberculata (teleomorph: Cochliobolus tuberculatus) |
| Didymella leaf spot | Didymella exitalis |
| Diplodia leaf spot or streak | Stenocarpella macrospora = Diplodialeaf macrospora |
| Brown stripe downy mildew | Sclerophthora rayssiae var. zeae |
| Crazy top downy mildew | Sclerophthora macrospora = Sclerospora macrospora |
| Green ear downy mildew (graminicola downy mildew) | Sclerospora graminicola |
| Leaf spots, minor | Alternaria alternata, Ascochyta maydis, A. tritici, A. zeicola, Bipolaris victoriae = Helminthosporium victoriae (teleomorph: Cochliobolus victoriae), C. sativus (anamorph: Bipolaris sorokiniana = H. sorokinianum = H. sativum), Epicoccum nigrum, Exserohilum prolatum = Drechslera prolata (teleomorph: Setosphaeria prolata) Graphium penicillioides, Leptosphaeria maydis, Leptothyrium zeae, Ophiosphaerella herpotricha, (anamorph: Scolecosporiella sp.), Paraphaeosphaeria michotii, Phoma sp., Septoria zeae, S. zeicola, S. zeina |
| Northern corn leaf blight (white blast, crown stalk rot, stripe) | Setosphaeria turcica (anamorph: Exserohilum turcicum = Helminthosporium turcicum) |
| Northern corn leaf spot Helminthosporium ear rot (race 1) | Cochliobolus carbonum (anamorph: Bipolaris zeicola = Helminthosporium carbonum) |
| Phaeosphaeria leaf spot | Phaeosphaeria maydis = Sphaerulina maydis |
| Rostratum leaf spot (Helminthosporium leaf disease, ear and stalk rot) | Setosphaeria rostrata, (anamorph: xserohilum rostratum = Helminthosporium rostratum) |
| Java downy mildew | Peronosclerospora maydis = Sclerospora maydis |
| Philippine downy mildew | Peronosclerospora philippinensis = Sclerospora philippinensis |
| Sorghum downy mildew | Peronosclerospora sorghi = Sclerospora sorghi |
| Spontaneum downy mildew | Peronosclerospora spontanea = Sclerospora spontanea |
| Sugarcane downy mildew | Peronosclerospora sacchari = Sclerospora sacchari |
| Sclerotium ear rot (southern blight) | Sclerotium rolfsii Sacc. (teleomorph: Athelia rolfsii) |
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae (anamorph: F. graminearum), Macrophomina phaseolina, Penicillium spp., Phomopsis sp., Pythium spp., Rhizoctonia solani, R. zeae, Sclerotium rolfsii, Spicaria sp. |
| Selenophoma leaf spot | Selenophoma sp. |
| Yellow leaf blight | Ascochyta ischaemi, Phyllosticta maydis (teleomorph: Mycosphaerella zeae-maydis) |
| Zonate leaf spot | Gloeocercospora sorghi |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo spec.*

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria (Stagonospora) nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae.*

Also preferred rust fungi are selected from the group of *Puccinia, Gymnosporangium, Juniperus, Cronartium, Hemlleia*, and *Uromyces*, preferably *Puccinia sorghi, Gymnosporangium juniperi-virginianae, Juniperus virginiana, Cronartium ribicola, Hemlleia vastatrix, Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus.*

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 3-10, 11, 13, 15, 17, 19, 21, 23, or 25 or a functional fragment thereof, or an orthologue or a paralogue thereof;
 (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 12, 14, 16, 18, 20, 22, 24, or 26, a functional fragment thereof, an orthologue or a paralogue thereof;
 (iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
 (iv) a nucleic acid encoding the same ACD protein as the ACD nucleic acids of (i) to (iii) above, but differing from the ACD nucleic acids of (i) to (iii) above due to the degeneracy of the genetic code operably linked with (b) a promoter and (c) a transcription termination sequence is a further embodiment of the invention.

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, or an orthologue or a paralogue thereof;
 (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof;
 (iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by (iv) a nucleic acid encoding the same ACD protein as the ACD nucleic acids of (i) to (iii) above, but differing from the ACD nucleic acids of (i) to (iii) above due to the degeneracy of the genetic code operably linked with (b) a promoter and (c) a transcription termination sequence is a further embodiment of the invention.

Furthermore, a recombinant vector construct is provided comprising:

(a) (i) a nucleic acid having at least 95%, at least 98%, at least 99% sequence identity, or even 100% sequence identity with SEQ ID NO: 1, 3-10, 11, 13, 15, 17, 19, 21, 23, or 25;

(ii) a nucleic acid coding for a protein having at least 95%, at least 98%, at least 99% sequence identity, or even 100% sequence identity with SEQ ID NO: 2, 12, 14, 16, 18, 20, 22, 24, or 26;

(iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by (iv) a nucleic acid encoding the same ACD protein as the ACD nucleic acids of (i) to (iii) above, but differing from the ACD nucleic acids of (i) to (iii) above due to the degeneracy of the genetic code operably linked with (b) a promoter and (c) a transcription termination sequence is a further embodiment of the invention.

Furthermore, a recombinant vector construct is provided comprising:

(a) (i) a nucleic acid having at least 95%, at least 98%, at least 99% sequence identity, or even 100% sequence identity with SEQ ID NO: 1;

(ii) a nucleic acid coding for a protein having at least 95%, at least 98%, at least 99% sequence identity, or even 100% sequence identity with SEQ ID NO: 2;

(iii) a nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by (iv) a nucleic acid encoding the same ACD protein as the ACD nucleic acids of (i) to (iii) above, but differing from the ACD nucleic acids of (i) to (iii) above due to the degeneracy of the genetic code operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter. A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the ACD protein takes place in a constitutive or tissue-specific manner. In especially preferred embodiments, an essentially pathogen-induced increase in the protein amount and/or protein activity takes place, for example by recombinant expression of the ACD nucleic acid under the control of a fungal-inducable promoter. In particular, the expression of the ACD nucleic acid takes place on fungal infected sites, where, however, preferably the expression of the ACD nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene)

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5(=GstA1); acc. X56012; Dudler & Schweizer,
GLP4, acc. AJ310534; Wei Y., Zhang Z., Andersen C. H., Schmelzer E., Gregersen P. L.,
Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphat translocator promoter (Accession NM_123979)
Act1 promoter:—*Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the ACD protein takes place in a constitutive or tissue-specific manner. In especially preferred embodiments, an essentially pathogen-induced increase in the protein quantity or protein function takes place, for example by exogenous expression of the ACD nucleic acid under the control of a fungal-inducible promoter. In particular, the expression of the ACD nucleic acid takes place on fungal infected sites, where, however, preferably the expression of the ACD nucleic acid sequence remains essentially unchanged in tissues not infected by fungus. In preferred embodiments, the protein amount of a ACD protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the ACD nucleic acid.

A preferred embodiment is a transgenic plant, transgenic plant part, or transgenic plant cell overexpressing an exogenous ACD protein. Preferably, the ACD protein overexpressed in the plant, plant part or plant cell is encoded by (i) an exogenous nucleic acid having at least 60% identity with SEQ ID NO: 1, 3-10, 11, 13, 15, 17, 19, 21, 23, or 25 or a functional fragment, thereof, an orthologue or a paralogue thereof; or by
(ii) an exogenous nucleic acid encoding a protein having at least 60% identity with SEQ ID NO: 2, 12, 14, 16, 18, 20, 22, 24, or 26, a functional fragment thereof, an orthologue or a paralogue thereof;
(iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by
(iv) an exogenous nucleic acid encoding the same ACD protein as the ACD nucleic acids of (i) to (iii) above, but differing from the ACD nucleic acids of (i) to (iii) above due to the degeneracy of the genetic code.

A preferred embodiment is a transgenic plant, transgenic plant part, or transgenic plant cell overexpressing an exogenous ACD protein. Preferably, the ACD protein overexpressed in the plant, plant part or plant cell is encoded by
(i) an exogenous nucleic acid having at least 60% identity with SEQ ID NO: 1 or a functional fragment, thereof, an orthologue or a paralogue thereof; or by
(ii) an exogenous nucleic acid encoding a protein having at least 60% identity with SEQ ID NO: 2, a functional fragment thereof, an orthologue or a paralogue thereof;
(iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants. Most preferably, the exogenous nucleic acid has at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2; and/or by
(iv) a nucleic acid encoding the same ACD protein as the ACD nucleic acids of (i) to (iii) above, but differing from the ACD nucleic acids of (i) to (iii) above due to the degeneracy of the genetic code.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*.

The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the ACD nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably against fungal pathogens of the family Phacopsoraceae, more preferably against fungal pathogens of the genus *Phacopsora*, most preferably against *Phakopsora pachyrhizi* (Sydow) and *Phakopsora meibomiae* (Arthur), also known as soybean rust. Preferably, resistance against *Phakopsora pachyrhizi* (Sydow) and/or *Phakopsora meibomiae* (Arthur) is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. *axiphium* Alef emend. C.O. Lehm), also called snow pea, edible-podded pea or mangetout, (*Pisum granda sneida* L. convar. *sneidulo* p. *shneiderium*)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

Further preferred is a plant selected from plant is selected from the group consisting of beans, soya, pea, clover, kudzu, lucerne, lentils, lupins, vetches, and groundnut. Most preferably, the plant, plant part, or plant cell is or is derived from soy.

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to a ACD nucleic acid, which is preferably SEQ ID NO: 1, and
a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step (c) expressing the ACD protein, preferably encoded by
   (i) an exogenous nucleic acid having at least 60% identity with SEQ ID NO: 1, 3-10, 11, 13, 15, 17, 19, 21, 23, or 25, a functional fragment thereof, an orthologue or a paralogue thereof;
   (ii) an exogenous nucleic acid encoding a protein having at least 60% identity with SEQ ID NO: 2, 12, 14, 16, 18, 20, 22, 24, or 26, or a functional fragment thereof, an orthologue or a paralogue thereof;
   (iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
   (iv) an exogenous nucleic acid encoding the same ACD protein as the ACD nucleic acids of (i) to (iii) above, but differing from the ACD nucleic acids of (i) to (iii) above due to the degeneracy of the genetic code.

Preferably, the method for the production of the transgenic plant, transgenic plant part, or transgenic plant cell further comprises the step
(c) expressing the ACD protein, preferably encoded by
  (i) an exogenous nucleic acid having at least 60% identity with SEQ ID NO: 1, a functional fragment thereof, an orthologue or a paralogue thereof;
  (ii) an exogenous nucleic acid encoding a protein having at least 60% identity with SEQ ID NO: 2, or a functional fragment thereof, an orthologue or a paralogue thereof;
  (iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
  (iv) an exogenous nucleic acid encoding the same ACD protein as the ACD nucleic acids of (i) to (iii) above, but differing from the ACD nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
  (i) the exogenous nucleic acid having at least 60% identity with SEQ ID NO: 1, 3-10, 11, 13, 15, 17, 19, 21, 23, or 25, a functional fragment thereof, an orthologue or a paralogue thereof;
  (ii) the exogenous nucleic acid encoding a protein having at least 60% identity with SEQ ID NO: 2, 12, 14, 16, 18, 20, 22, 24, or 26, or a functional fragment thereof, an orthologue or a paralogue thereof;
  (iii) the exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
  (iv) the exogenous nucleic acid encoding the same ACD protein as the ACD nucleic acids of (i) to (iii) above, but differing from the ACD nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
  (i) the exogenous nucleic acid having at least 60% identity with SEQ ID NO: 1, a functional fragment thereof, an orthologue or a paralogue thereof;
  (ii) the exogenous nucleic acid encoding a protein having at least 60% identity with SEQ ID NO: 2, or a functional fragment thereof, an orthologue or a paralogue thereof;
  (iii) the exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
  (iv) the exogenous nucleic acid encoding the same ACD protein as the ACD nucleic acids of (i) to (iii) above, but differing from the ACD nucleic acids of (i) to (iii) above due to the degeneracy of the genetic code.

The transgenic plants may be selected by known methods as described above (e.g., by screening for the presence of one or more markers which are encoded by plant-expressible genes co-transferred with the ACD gene or by directly screening for the ACD nucleic acid).

Furthermore, the use of the exogenous ACD nucleic acid or the recombinant vector construct comprising the ACD nucleic acid for the transformation of a plant, plant part, or plant cell to provide a fungal resistant plant, plant part, or plant cell is provided.

Harvestable parts of the transgenic plant according to the present invention are part of the invention. The harvestable parts may be seeds, roots, leaves and/or flowers comprising the ACD nucleic acid or ACD protein or parts thereof. Preferred parts of soy plants are soy beans comprising the ACD nucleic acid or ACD protein.

Products derived from a transgenic plant according to the present invention, parts thereof or harvestable parts thereof are part of the invention. A preferred product is soybean meal or soybean oil.

Preferably, the harvestable part of the transgenic plant or the product derived from the transgenic plant comprises an exogenous ACD nucleic acid, wherein the exogenous ACD nucleic acid is selected from the group consisting of:
  (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 3-10, 11, 13, 15, 17, 19, 21, 23, or 25, a functional fragment thereof, or an orthologue or a paralogue thereof; or by
  (ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 12, 14, 16, 18, 20, 22, 24, or 26, a functional fragment thereof, an orthologue or a paralogue thereof,
  (iii) an exogenous nucleic acid capable of hybridizing under stringent conditions with any of the nucleic acids according to (i) or (ii) or a complementary sequence (complement) thereof, and which preferably encodes a ACD protein that has essentially the same biological activity as an ACD protein encoded by SEQ ID NO: 2; preferably the encoded ACD protein confers enhanced fungal resistance relative to control plants; or by
  (iv) an exogenous nucleic acid encoding the same ACD protein as the ACD nucleic acids of (i) to (iii) above, but differing from the ACD nucleic acids of (i) to (iii) above due to the degeneracy of the genetic code;
or wherein the harvestable part of the transgenic plant or the product derived from the transgenic plant comprises an ACD protein encoded by any one of the ACD nucleic acids of (i) to (iv).

In one embodiment the method for the production of a product comprises a) growing the plants of the invention or obtainable by the methods of invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably, the product obtained by said method comprises an exogenous ACD nucleic acid, wherein the exogenous ACD nucleic acid is selected from the group consisting of:
(i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 3-10, 11, 13, 15, 17, 19, 21, 23, or 25, a functional fragment thereof, or an orthologue or a paralogue thereof; or by
(ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 12, 14, 16, 18, 20, 22, 24, or 26, a functional fragment thereof, an orthologue or a paralogue thereof, or by
(iii) an exogenous nucleic acid capable of hybridizing under stringent conditions with any of the nucleic acids according to (i) or (ii) or a complementary sequence (complement) thereof, and which preferably encodes a ACD protein that has essentially the same biological activity as an ACD protein encoded by SEQ ID NO: 2; preferably the encoded ACD protein confers enhanced fungal resistance relative to control plants; or by
(iv) an exogenous nucleic acid encoding the same ACD protein as the ACD nucleic acids of (i) to (iii) above, but differing from the ACD nucleic acids of (i) to (iii) above due to the degeneracy of the genetic code;
or wherein the product obtained by said method comprises an ACD protein encoded by any one of the ACD nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the ACD nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a ACD protein, preferably encoded by
  (i) an exogenous nucleic acid having at least 60% identity with SEQ ID NO: 1, 3-10, 11, 13, 15, 17, 19, 21, 23, or 25, a functional fragment thereof, an orthologue or a paralogue thereof;
  (ii) an exogenous nucleic acid encoding a protein having at least 60% identity with SEQ ID NO: 2, 12, 14, 16, 18, 20, 22, 24, or 26, or a functional fragment thereof, an orthologue or a paralogue thereof;
  (iii) an exogenous nucleic acid capable of hybridizing under stringent conditions with any of the nucleic acids according to (i) or (ii) or a complement thereof, and which preferably encodes a ACD protein that has essentially the same biological activity as an ACD protein encoded by SEQ ID NO: 2; preferably the encoded ACD protein confers enhanced fungal resistance relative to control plants; and/or by
  (iv) an exogenous nucleic acid encoding the same ACD protein as the ACD nucleic acids of (i) to (iii) above, but differing from the ACD nucleic acids of (i) to (iii) above due to the degeneracy of the genetic code.

The transgenic plants may be selected by known methods as described above (e.g., by screening for the presence of one or more markers which are encoded by plant-expressible genes co-transferred with the ACD gene or screening for the ACD nucleic acid itself).

According to the present invention, the introduced ACD nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous ACD nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

FIGURES

FIG. 1 shows the schematic illustration of mode of action of the ACD protein. The biosynthesis of ethylene in plants starts with the conversion of methionine to S-adenosyl-L-methionine (SAM) by SAM synthetase (SAMS). In a second step SAM is converted to 1-aminocyclopropane-1-carboxylic acid (ACC) by the enzyme ACC synthase (ACS). This step is the rate limiting step in the ethylene production in the plant and therefore the tight regulation of this enzyme is key for ethylene biosynthesis. In a final step ACC-oxidase (ACO) forms ethylene from ACC and oxygen. Binding of ET leads by the ethylene receptor activates the ethylene signaling cascade leading to the expression of ET dependent genes.

FIG. 3 shows the full-length-sequence of the ACD-gene from *Pseudomonas* spec. having SEQ ID NO: 1.

FIG. 4 shows the sequence of the ACD-protein (SEQ ID NO: 2).

FIG. 5 shows the result of the scoring of 13 transgenic soy plants expressing the ACD overexpression vector construct. $T_0$ soybean plants expressing ACD protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 13 soybean $T_0$ plants expressing ACD (expression checked by RT-PCR) were evaluated in parallel to non-transgenic control plants. The average of the diseased leaf area is shown in FIG. 5. Overexpression of ACD reduces the diseased leaf area in comparison to non-transgenic control plants by 42%.

FIG. 6 contains a brief description of the sequences of the sequence listing.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNAs of all genes mentioned in this application were generated by DNA synthesis (Geneart, Regensburg, Germany).

The ACD cDNA were synthesized in a way that a attB1-recombination site (Gateway system, Invitrogen, Life Technologies, Carlsbad, Calif., USA) is located in front of the start-ATG and a attB2 recombination site is located directly downstream of the stop-codon. The synthesized cDNA were transferred to a pENTRY-B vector by using the BP reaction (Gateway system, Invitrogen, Life Technologies, Carlsbad, Calif., USA) according to the protocol provided by the supplier. To obtain the binary plant transformation vector, a triple LR reaction (Gateway system, Invitrogen, Life Technologies, Carlsbad, Calif., USA) was performed according to manufacturers protocol by using a pENTRY-A vector containing a parsley ubiquitine promoter, the cDNA in a pENTRY-B vector and a pENTRY-C vector containing a *Solanum tuberosum* StCAT-pA terminator. As target a binary pDEST vector was used which is composed of: (1) a Spectinomycin/Streptomycin resistance cassette for bacterial selection (2) a pVS1 origin for replication in Agrobacteria (3) a pBR322 origin of replication for stable maintenance in *E. coli* and (4) between the right and left border an AHAS selection under control of a pcUbi-promoter (FIG. 4). The recombination reaction was transformed into *E. coli* (DH5alpha), mini-prepped and screened by specific restriction digestions. A positive clone from each vector construct was sequenced and submitted soy transformation.

Example 3: Soy Transformation

Figure 1:
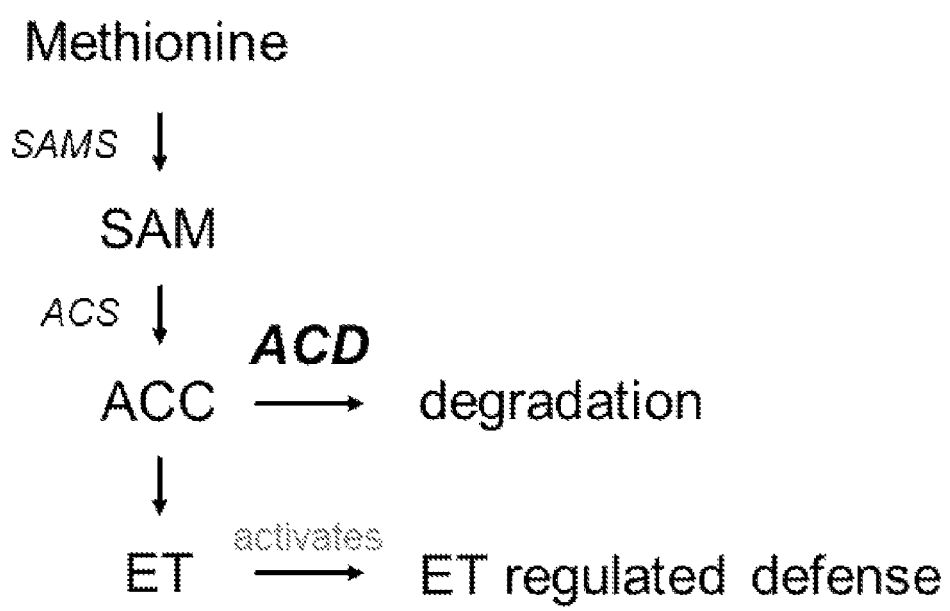
Figure 2:
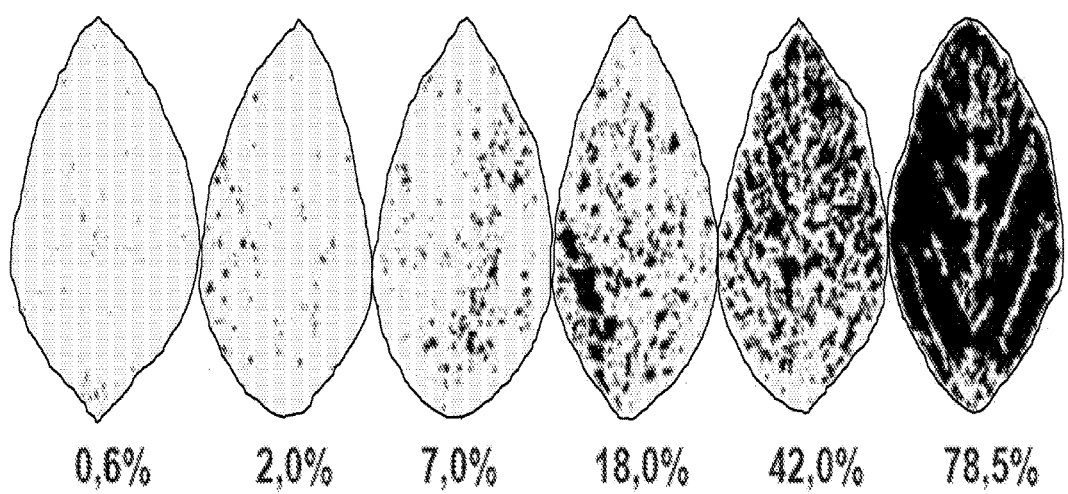
FIG. 2 shows the scoring system used to determine the level of diseased leaf area of wildtype and transgenic soy plants against the rust fungus *P. pachyrhizi.*
Figure 5:
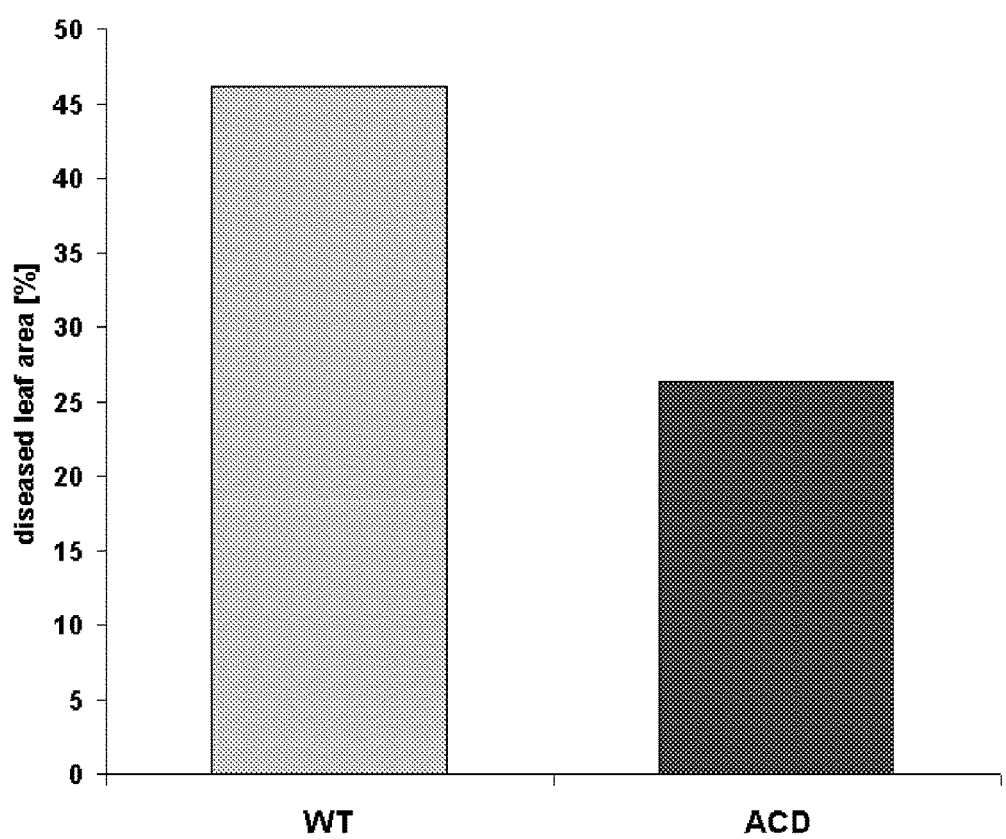

The expression vector constructs (see example 2) were transformed into soy.

3.1 Sterilization and Germination of Soy Seeds

Virtually any seed of any soy variety can be employed in the method of the invention. A variety of soycultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/$m^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3. and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were sub-cultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soy-plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the Agrobacterium suspension immediately after explant preparation. After inoculation, the explants are blotted onto sterile filter paper to remove excess Agrobacterium culture and place explants with the wounded side in contact with a round 7 cm Whatman paper overlaying the solid CCM medium (see above). This filter paper prevents A. tumefaciens overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the Agrobacterium. Therefore, a 0.5 cm explant included the stem and a bud.

Once cut, the explants were immediately placed in the Agrobacterium suspension for 20 to 30 minutes. After inoculation, the explants were blotted onto sterile filter paper to remove excess Agrobacterium culture then placed almost completely immersed in solid CCM or on top of a round 7 cm filter paper overlaying the solid CCM, depending on the Agrobacterium strain. This filter paper prevents Agrobacterium overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess Agrobacterium) (SIM, see Olhoft et al 2007 A novel Agrobacterium rhizogenes-mediated transformation method of soy using primary-node explants from seedlings In Vitro Cell. Dev. Biol.—Plant (2007) 43:536-549; to remove excess Agrobacterium) or Modwash medium (1× B5 major salts, 1× B5 minor salts, 1×MSIII iron, 3% Sucrose, 1× B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2 s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel Agrobacterium rhizogenes-mediated transformation method of soy using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with Agrobacterium tumefaciens transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Recovery of Clones 2-3 clones per $T_0$ event were potted into small 6 cm pots. For recovery the clones were kept for 12-18 days in the phytochamber (16 h-day- and 8 h-night-Rhythm at a temperature of 16°-22° C. and a humidity of 75%).

4.2 Inoculation

The plants were inoculated with *P. pachyrhizi*.

In order to obtain appropriate spore material for the inoculation, soy leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×105 spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 2).

$T_0$ soybean plants expressing ACD protein were inoculated with spores of *Phakopsora pachyrhizi*. The macroscopic disease symptoms of soy against *P. pachyrhizi* of 13 $T_0$ soybean plants were scored 14 days after inoculation.

The average of the percentage of the leaf area showing fungal colonies or strong yellowing/browning on all leaves was considered as diseased leaf area. At all 13 soybean $T_0$ plants expressing ACD (expression checked by RT-PCR) were evaluated in parallel to non-transgenic control plants. Clones from non-transgenic soy plants were used as control. The average of the diseased leaf area is shown in FIG. 5 for plants expressing recombinant ACD compared with wild-type plants. Overexpression of ACD reduces the diseased leaf area in comparison to non-transgenic control plants by 42% in average over all events generated. This data clearly indicate that the in planta expression of the ACD expression vector construct lead to a lower disease scoring of transgenic plants compared to non-transgenic controls. So, the expression of ACD in soy increases the resistance of soy against soybean rust.

The invention claimed is:

1. A method for preventing, reducing, or delaying *Phakopsora* infection in a soybean plant, a soybean plant part, or a soybean plant cell, the method comprising
    (a) providing a transgenic soybean plant, transgenic soybean plant part, or transgenic soybean plant cell with an exogenous nucleic acid encoding an aminocyclopropane carboxylic acid deaminase (ACD) protein having an amino acid sequence with at least 80% identity to SEQ ID NO:2, wherein the ACD protein confers increased resistance against *Phakopsora* thereto in comparison to a wild type soybean plant, wild type soybean plant part or wild type soybean plant cell; and
    (b) growing the transgenic soybean plant, transgenic soybean plant part, or transgenic soybean plant cell in the presence of a fungal pathogen of the genus *Phakopsora*, wherein *Phakopsora* infection is prevented, reduced, or delayed in the transgenic soybean plant, transgenic soybean plant part, or transgenic soybean plant cell as compared to a wild type soybean plant, wild type soybean plant part, or wild type soybean plant cell.

2. A recombinant vector construct comprising, in operable linkage:
    (a) a nucleic acid encoding an ACD protein having an amino acid sequence with at least 80% identity to SEQ ID NO: 2;
    (b) a heterologous promoter, wherein the promoter is a fungal-inducible promoter or a mesophyll-specific promoter and (c) a transcription termination sequence,
wherein expression of said recombinant vector construct in a soybean plant, soybean plant part, or soybean plant cell confers increased resistance against *Phakopsora* thereto in comparison to a wild type soybean plant, wild type soybean plant part or wild type soybean plant cell.

3. The method of claim 1, wherein the exogenous nucleic acid is in functional linkage with a promoter, and the promoter is a constitutive promoter, a pathogen-inducible promoter, a mesophyll-specific promoter, or an epidermis specific-promoter.

4. A transgenic soybean plant, transgenic soybean plant part, or transgenic soybean plant cell comprising an exogenous nucleic acid encoding an ACD protein having an amino acid sequence with at least 80% identity to SEQ ID NO:2, wherein the ACD protein confers increased resistance against *Phakopsora* thereto in comparison to a wild type soybean plant, wild type soybean plant part or wild type soybean plant cell.

5. A method for the production of a transgenic plant, transgenic plant part, or transgenic plant cell having increased fungal resistance, comprising:
   (a) introducing the recombinant vector construct of claim 2 into a plant, a plant part, or a plant cell;
   (b) generating a transgenic plant, transgenic plant part, or transgenic plant cell from the plant, plant part or plant cell; and
   (c) expressing the ACD protein.

6. The method of claim 5, further comprising the step of harvesting the seeds of the transgenic plant and planting the seeds and growing the seeds to plants, wherein the grown plants comprise the recombinant vector construct.

7. A harvestable part of the transgenic plant of claim 4, wherein the harvestable part of the transgenic plant comprises the exogenous nucleic acid.

8. A product derived from the plant of claim 4, wherein the product comprises the exogenous nucleic acid.

9. A method for the production of a product comprising:
   a) growing the plant of claim 4; and
   b) producing said product from or by the plant or a part thereof,
   wherein the product comprises the exogenous nucleic acid.

10. The method of claim 9 comprising:
    a) growing the plant and removing the harvestable parts from the plants; and
    b) producing said product from or by the harvestable parts of the plant,
    wherein the product comprises the exogenous nucleic acid.

11. The method of claim 1, wherein the resistance against soybean rust is resistance against *Phakopsora meibomiae*, *Phakopsora pachyrhizi*, or combinations thereof.

12. A method for breeding a fungal resistant plant comprising:
    (a) crossing the plant of claim 4 with a second plant;
    (b) obtaining seeds from the cross of step (a);
    (c) planting said seeds and growing the seeds to plants; and
    (d) selecting, from said plants, plants expressing the ACD protein.

13. The method of claim 1, wherein all of the amino acid residues in the ACD protein not identical to SEQ ID NO: 2 are conservative amino acid substitutions.

14. The method of claim 1, wherein the exogenous nucleic acid encodes an ACD protein with at least 85% identity to SEQ ID NO: 2.

15. The method of claim 1, wherein the exogenous nucleic acid encodes an ACD protein with at least 90% identity to SEQ ID NO: 2.

16. The method of claim 1, wherein the exogenous nucleic acid encodes an ACD protein with at least 95% identity to SEQ ID NO: 2.

* * * * *

UNITED STATES PATENT AND TRADEMARK OFFICE
CERTIFICATE OF CORRECTION

PATENT NO. : 10,450,582 B2
APPLICATION NO. : 15/614082
DATED : October 22, 2019
INVENTOR(S) : Holger Schultheiss et al.

It is certified that error appears in the above-identified patent and that said Letters Patent is hereby corrected as shown below:

In the Claims

Column 79, Lines 59-60, Claim 1, "aminocvclopropane" should be -- aminocyclopropane --.

Signed and Sealed this
Sixteenth Day of April, 2024

Katherine Kelly Vidal
*Director of the United States Patent and Trademark Office*